US006168839B1

(12) United States Patent
Fujita et al.

(10) Patent No.: US 6,168,839 B1
(45) Date of Patent: Jan. 2, 2001

(54) CYCLOHEXANE DERIVATIVES, LIQUID-CRYSTAL COMPOSITION, AND LIQUID-CRYSTAL DISPLAY ELEMENT

(75) Inventors: Atsuko Fujita; Shuichi Matsui; Kazutoshi Miyazawa; Hiroyuki Takeuchi; Fusayuki Takeshita; Etsuo Nakagawa, all of Chiba (JP)

(73) Assignee: Chisso Corporation, Osaka (JP)

( * ) Notice: Under 35 U.S.C. 154(b), the term of this patent shall be extended for 0 days.

(21) Appl. No.: 09/331,428

(22) PCT Filed: Dec. 16, 1997

(86) PCT No.: PCT/JP97/04632

§ 371 Date: Jun. 21, 1999

§ 102(e) Date: Jun. 21, 1999

(87) PCT Pub. No.: WO98/27048

PCT Pub. Date: Jun. 25, 1998

(30) Foreign Application Priority Data

Dec. 19, 1996 (JP) .................................................. 8-354319

(51) Int. Cl.[7] .......................... C09K 19/30; C07C 69/74; C07C 255/31; C07C 57/26; C07C 59/62
(52) U.S. Cl. ................... 428/1.1; 252/299.63; 558/430; 560/126; 560/128
(58) Field of Search ................ 252/299.63, 299.01; 428/1.1; 558/430; 560/126, 128

(56) References Cited

FOREIGN PATENT DOCUMENTS 54-151951   11/1979   (JP) .
2-278230    11/1990   (JP) .
6-57252      3/1994   (JP) .

OTHER PUBLICATIONS

Chem. abstr., vol. 74, No. 19, May 10, 1971 (Columbus, OH, USA), p. 464, the abstract No. 99493a, Vidugiriene, V. et al., "Addition of sulfenyl chlorides to unsaturated 3–cyclohexenic acids and their derivatives." Liet, TSR Mokslu Akad. darb., Ser. B 1970 (4) 171–7 (Russ).

Flussige Kristalle in Tabellen, VEB Deutscher Verlagfur Grundstoffindustrie (1974), p. 34.

*Primary Examiner*—Shean C. Wu
(74) *Attorney, Agent, or Firm*—Wenderoth, Lind & Ponack, L.L.P.

(57) ABSTRACT

Novel liquid crystalline compounds which have a wide temperature range of liquid crystal phase, are excellent in miscibility with other liquid crystalline compounds, have a low viscosity, are low in toxicity, and are safe; liquid crystal compositions comprising the liquid crystalline compound; and liquid crystal display devices fabricated by using the composition are provided; and the compounds are cyclohexane derivatives expressed by the general formula (1)

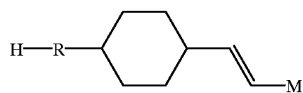

(1)

wherein R represents an alkylene chain having 2 to 10 carbon atoms in which alkylene chain ethylene group ($-CH_2CH_2-$) may be replaced by ethenylene group ($-CH=CH-$) or methylenoxy group ($-OCH_2-$); and M represents COOH or CN group.

14 Claims, No Drawings

CYCLOHEXANE DERIVATIVES, LIQUID-CRYSTAL COMPOSITION, AND LIQUID-CRYSTAL DISPLAY ELEMENT

This application is a 371 of PCT/JP97/04632, filed Dec. 16, 1997.

TECHNICAL FIELD

The present invention relates to novel liquid crystalline compounds, liquid crystal compositions comprising the compound, and liquid crystal display devices fabricated by using the composition.

BACKGROUND ART

Display devices employing such characteristics as optical (refractive) anisotropy or dielectric anisotropy of liquid crystal substances have widely been utilized for watches, tabletop calculators, or the likes. While the liquid crystal phase exhibited by the liquid crystal substances includes nematic liquid crystal phase, smectic liquid crystal phase, and cholesteric liquid crystal phase, nematic liquid crystal phase is most general in practical use. Display mode employing the nematic liquid crystal phase includes TN (twisted nematic) type, DS (dynamic scattering) type, guest-host type, and DAP (deformation of aligned phase) type.

As liquid crystalline compounds (including liquid crystal substances and compounds which do not exhibit liquid crystal phase but are effective as component of liquid crystal compositions) used for these display modes, many compounds have heretofore been developed. However, no compounds have been filled in display devices in a state of single component and actually used up to now. The reason is that whereas, as the liquid crystalline compounds expected to be used as liquid crystal materials for display devices, compounds which exhibit a liquid crystal phase at a temperature in a range as wide as possible with room temperature, at which display devices are used at a highest frequency, being its center are desired, the compounds must be sufficiently stable against environmental factors at the time of use and the compounds must have physical properties sufficient to make display devices be driven, liquid it crystalline compounds which satisfy these requirements as single compound have not yet been found.

Accordingly, at present, a plural number of liquid crystalline compounds are mixed to prepare compositions having such characteristics as described above and the compositions are put to practical use as liquid crystal material.

While it is generally considered to be necessary that these liquid crystal compositions are stable against moisture, light, heat, and air which usually exist under conditions wherein the compositions are used, that the compositions are stable against electric field and electromagnetic radiation, and that liquid crystalline compounds to be mixed to prepare the compositions are stable against each other, and are safe, the following characteristics are further desired depending on the purposes of the compositions.

For instance, liquid crystal compositions for liquid crystal display devices of TN mode which are most widely used are considered to be necessary to have a low viscosity, wide temperature range of liquid crystal phase, and large dielectric anisotropy value (Δε) in addition to the characteristics described above. In order to satisfy the requirement, attempts in which liquid crystal compositions having each different characteristics are mixed have been made. However, when simple substances of liquid crystalline compound having varied characteristics are mixed, liquid crystal compositions to be obtained come to have a large dependency on frequency and temperature, and production of display devices which enable uniform display regardless of the changes in usage conditions becomes impossible.

As components of liquid crystal compositions for nematic display mode, liquid crystalline compounds having a rod-like molecular structure in which six-membered rings are linearly linked are ordinarily used, and characteristics such as temperature range of liquid crystal phase and viscosity of the compounds are known to be approximately determined by the number of the six-membered rings described above.

That is, as the number of six-membered ring decreases, the viscosity generally reduces but the temperature range of liquid crystal phase narrows. On the contrary, as the number of six-membered ring increases, the viscosity increases but the temperature range of liquid crystal phase widens. Particularly in the case where the number of six-membered ring is 4 or more the temperature range of liquid crystal phase remarkably widens. Thus, such case is desirable, but on the other side, the viscosity considerably increases.

Accordingly, liquid crystalline compounds which exhibit a low value as to the viscosity similar to that of the liquid crystalline compounds having a small number of the rings in spite of having such a wide temperature range of liquid crystal phase are desired, and several compounds have been developed heretofore. For instance, cyclohexanecarboxylic acid derivatives expressed by the formula (10) are known as the compound having a comparatively wide temperature range of liquid crystal phase and a low viscosity (Flussige Kristalle in Tabellen, VEB Deutscher Verlagfur Grundstoffindustrie (1974) 34 p and Laid-open Japanese Patent Publication No. Sho 54-151951). However, the derivatives have been found out to have acute toxicity (in this connection, it has been published that the derivatives are extremely high in toxicity such that their half lethal dose ($LD_{50}$) caused by acute toxicity is 18 mg/kg, although it is a result of intravenous injection to mice), and thus it is not preferable from the aspect of environmental safety to fill the derivatives in practical panels and use them.

Further, whereas benzoic acid derivatives expressed by the formula (11) are known as the compounds having a low viscosity (Laid-open Japanese Patent Publication No. Hei 6-57252), the derivatives do not have a wide temperature range of liquid crystal phase such an extent as necessary to withstand practical use.

(10)

(11)

DISCLOSURE OF THE INVENTION

An object of the present invention is to solve the defects in conventional technology described above. Another object of the present invention is to provide cyclohexane derivatives of novel liquid crystalline compounds having a wide temperature range of liquid crystal phase, being excellent in miscibility with other liquid crystalline compounds, having a low viscosity, being low in toxicity, and being safe; to provide liquid crystal compositions comprising the compound, and to provide liquid crystal display devices fabricated by using the composition.

For achieving the objects described above, the present invention is summarized as follows:

(1) A cyclohexane derivative expressed by the general formula (1)

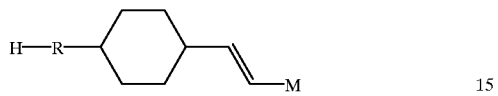
(1)

wherein R represents an alkylene chain having 2 to 10 carbon atoms in which alkylene chain ethylene group (—CH$_2$CH$_2$—) may be replaced by ethenylene group (—CH═CH—) or methylenoxy group (—OCH$_2$—); and M represents COOH or CN group.

(2) The cyclohexane derivative recited in paragraph (1) above wherein M is COOH group.

(3) The cyclohexane derivative recited in paragraph (1) above wherein M is CN group.

(4) The cyclohexane derivative recited in paragraph (1) above wherein R is an alkylene chain having 2 to 10 carbon atoms.

(5) The cyclohexane derivative recited in paragraph (2) above wherein R is an alkylene chain having 2 to 10 carbon atoms.

(6) The cyclohexane derivative recited in paragraph (1) above wherein R is an alkenylene group having 2 to 10 carbon atoms.

(7) A liquid crystal composition comprising at least one cyclohexane derivative recited in any one of paragraphs (1) to (6) above.

(8) A liquid crystal composition comprising, as a first component, at least one cyclohexane derivative recited in any one of paragraphs (1) to (6) above, and comprising, as a second component, at least one compound selected from the group consisting of the compounds expressed by any one of the general formulas (2), (3), and (4)

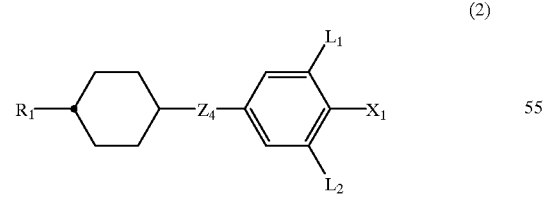
(2)

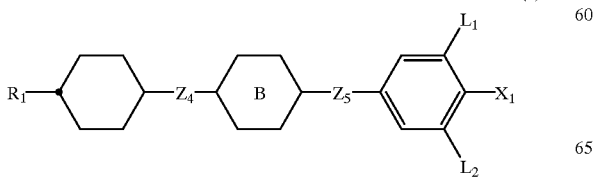
(3)

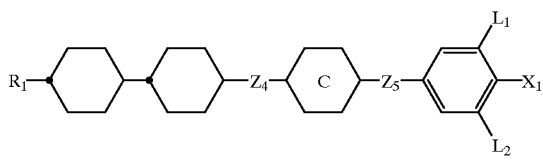
(4)

wherein R$_1$, X$_1$, L$_1$, L$_2$, Z$_4$, Z$_5$ may be the same or different among the formulas; R$_1$ represents an alkyl group having 1 to 10 carbon atoms in which alkyl group one or not adjacent two or more methylene groups may be replaced by oxygen atom or —CH═CH—, and any hydrogen atom may be replaced by fluorine atom; X$_1$ represents fluorine atom, chlorine atom, OCF$_3$, OCF$_2$H, CF$_3$, CF$_2$H, CFH$_2$, OCF$_2$CF$_2$H, or OCF$_2$CFHCF$_3$; L$_1$ and L$_2$ independently represent hydrogen atom or fluorine atom; Z$_4$ and Z$_5$ independently represent 1,2-ethylene group, 1,4-butylene group, —COO—, —CF$_2$O—, —OCF$_2$—, —CH═CH—, or a covalent bond; ring B represents trans-1,4-cyclohexylene or 1,3-dioxane-2,5-diyl, or 1,4-phenylene in which hydrogen atom on the ring may be replaced by fluorine atom; ring C represents trans-1,4-cyclohexylene, or 1,4-phenylene in which hydrogen atom on the ring may be replaced by fluorine atom; and each of the atoms which constitute these compounds may be selected from its isotopes.

(9) A liquid crystal composition comprising, as a first component, at least one cyclohexane derivative recited in any one of paragraphs (1) to (6) above, and comprising, as a second component, at least one compound selected from the group consisting of the compounds expressed by the general formula (5) or (6)

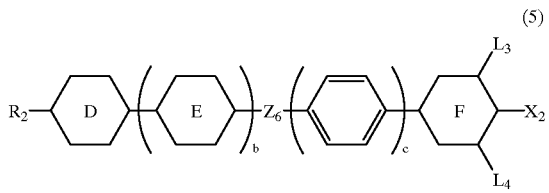
(5)

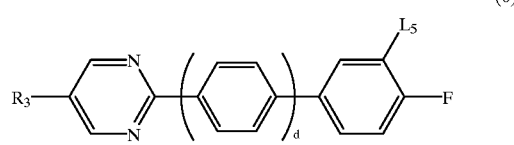
(6)

wherein R$_2$ and R$_3$ independently represent an alkyl group having 1 to 10 carbon atoms in which alkyl group one or not-adjacent two or more methylene groups may be replaced by oxygen atom or —CH═CH—, and any hydrogen atom may be replaced by fluorine atom; X$_2$ represents —CN group or —C≡C—CN group; ring D represents trans-1,4-cyclohexylene, 1,4-phenylene, 1,3-dioxane-2,5-diyl, or pyrimidine-2,5-diyl; ring E represents trans-1,4-cyclohexylene, 1,4-phenylene in which hydrogen atom on the ring may be replaced by fluorine atom, or pyrimidine-2,5-diyl; ring F represents trans-1,4-cyclohexylene or 1,4-phenylene; Z$_6$ represents 1,2-ethylene group, —COO—, or a covalent bond; L$_3$, L$_4$, and L$_5$ independently represent hydrogen atom or fluorine atom; b, c, and d are independently 0 or 1; and in the compounds of each formulas, each atom which constitutes those compounds may be selected from its isotopes.

(10) A liquid crystal composition comprising, as a first component, at least one cyclohexane derivative recited in any one of paragraphs (1) to (6) above, comprising, as a second component, at least one compound selected from the group consisting of the compounds expressed by any one of the general formulas (2), (3), and (4) described above, and comprising, as third component, at least one compound selected from the group consisting of the compounds expressed by any one of the general formulas (7), (8), and (9)

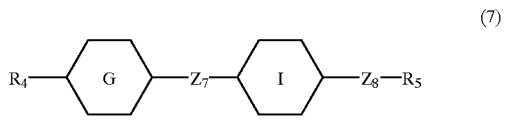

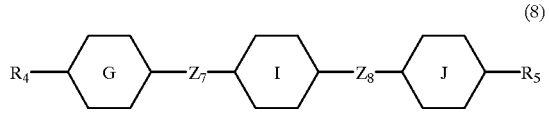

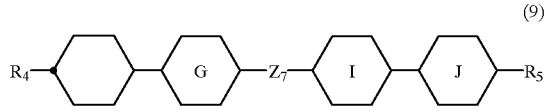

wherein $R_4$, $R_5$, ring G, ring I, and ring J may be the same or different among each of the formulas; $R_4$ and $R_5$ independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; ring G, ring I, and ring J independently represent trans-1, 4-cyclohexylene or pyrimidine-2,5-diyl, or 1,4-phenylene in which hydrogen atom on the ring may be replaced by fluorine atom; $Z_7$ and $Z_8$ independently represent —C≡C—, —COO—, —CH$_2$CH$_2$—, —CH=CH—, or a covalent bond; and in the compounds of each formulas, each atom which constitutes those compounds may be selected from its isotopes.

(11) A liquid crystal composition comprising, as a first compound, at least one cyclohexane derivative recited in in any one of paragraphs (1) to (6) above, comprising, as a second component, at least one compound selected from the group consisting of the compounds expressed by the formula (5) or (6) described above, and comprising, as a third component, at least one compound selected from the group consisting of the compounds expressed by any one of the general formulas (7), (8), and (9) described above.

(12) A liquid crystal composition comprising, as a first compound, at least one cyclohexane derivative recited in any of paragraphs (1) to (6) above, comprising, as a part of a second component, at least one compound selected from the group consisting of the compounds expressed by any one of the general formulas (2), (3), and (4) described above, comprising as another part of the second component, at least one compound selected from the group consisting of the compounds expressed by the formula (5) or (6) described above, and comprising, as a third component, at least one compound selected from the group consisting of the compounds expressed by any one of the general formulas (7), (8), and (9) described above.

(13) The liquid crystal composition recited in any one of paragraphs (7) to (12) wherein the liquid crystal composition further comprises an optically active compound.

(14) A liquid crystal display device fabricated by using a liquid crystal composition recited in any one of paragraphs (7) to (13) above.

BEST MODE FOR CARRYING OUT THE INVENTION

As will be clear from the general formula (1) described above, since cyclohexane derivatives which are liquid crystalline compounds of the present invention have a one-ring structure and are naturally small in the number of six-membered ring contained in the molecule compared with conventional liquid crystalline compounds, any of the cyclohexane derivatives exhibit a low viscosity. However, the cyclohexane derivative of the present invention further have a wide temperature range of liquid crystal phase in common with two-ring compounds ordinarily used, are safe since they do not have such a toxic as observed in cyclohexanecarboxylic acid derivatives, are excellent in miscibility with other liquid crystalline compounds, and are even chemically stable at the same time.

Liquid crystal compositions of the present invention comprise, as a first component, at least one liquid crystalline compound expressed by the general formula (1).

Its content is necessary to be in the range of 0.1 to 99.9% by weight based on the amount of liquid crystal composition for developing excellent characteristics.

While the liquid crystal composition of the present invention may comprise only the first component described above the compositions in which at least one compound selected from the group consisting of the compounds expressed by one of the general formulas (2), (3), and (4) described above (hereinafter referred to as second component A) and/or at least one compound selected from the group consisting of the compounds expressed by the general formula (5) or (6) described above (hereinafter referred to as second component B) are mixed as a second component in addition to the first component, or the compositions in which at least one compound selected from the group consisting of the compounds expressed by one of the general formulas (7), (8), and (9) described above are further mixed as a third component in addition to the first and second components are preferable. Besides, an optically active compound as another component, and a known compound may be mixed for the purpose of adjusting threshold voltage, temperature range of liquid crystal phase, optical anisotropy value (Δn), dielectric anisotropy value (Δε), and viscosity.

Among the second component A described above, the compounds expressed by one of the following formulas (2-1) to (2-9) can be mentioned as preferable examples of the ones included in the general formula (2), the compounds of one of the following formulas (3-1) to (3-69) can be mentioned as preferable examples of the ones included in the general formula (3), and the compounds of one of the following formulas (4-1) to (4-24) can be mentioned as preferable examples of the ones included in the general formula (4), respectively.

(2-1) 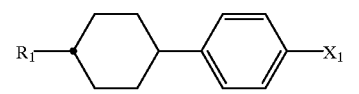
(2-2) 
(2-3) 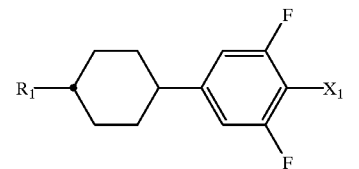
(2-4) 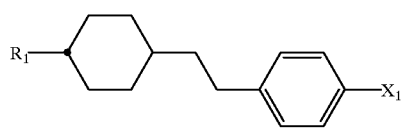
(2-5) 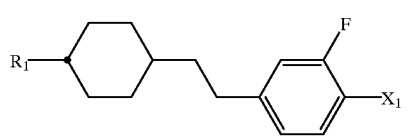
(2-6) 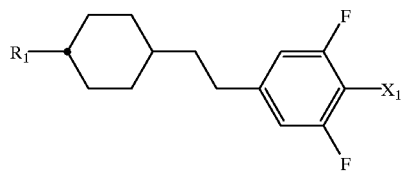
(2-7) 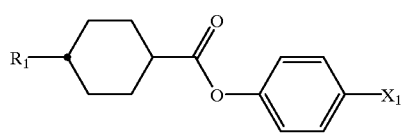
(2-8) 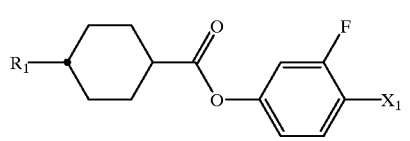
(2-9) 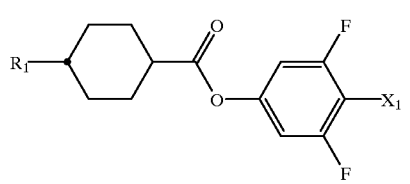
(3-1) 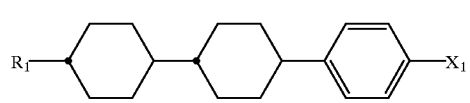
(3-2) 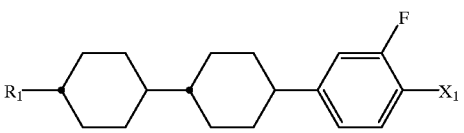
(3-3) 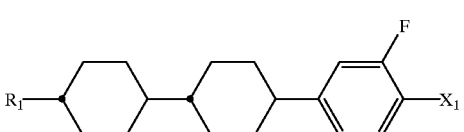
(3-4) 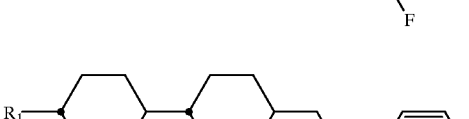
(3-5) 
(3-6) 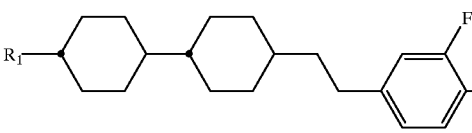
(3-7) 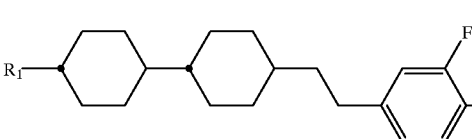
(3-8) 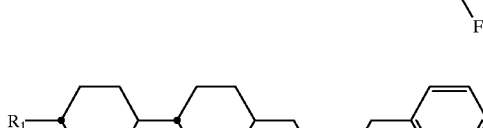
(3-9) 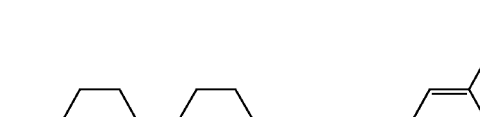
(3-10) 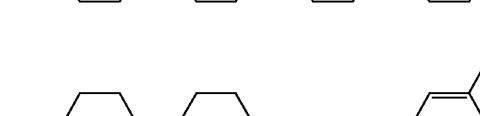
(3-11) 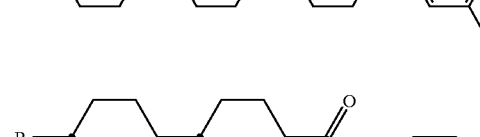

(3-12)
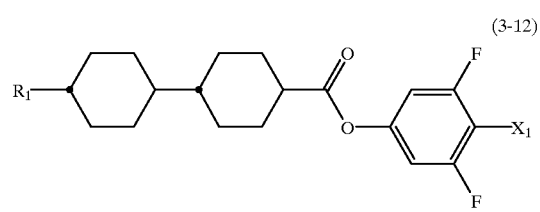
(3-13)
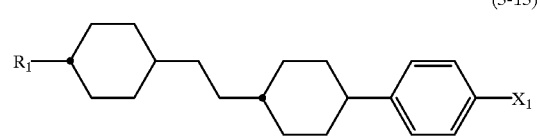
(3-14)
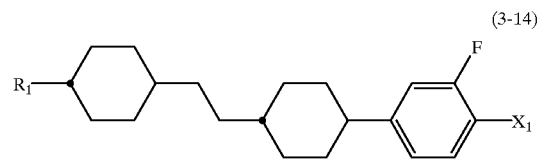
(3-15)
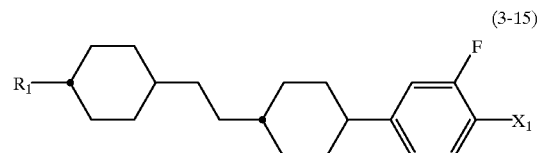
(3-16)
(3-17)
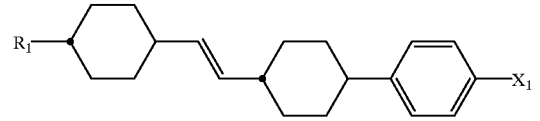
(3-18)
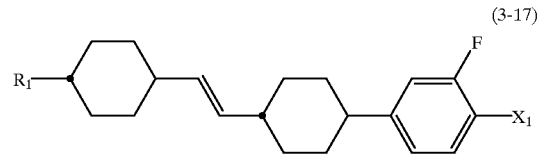
(3-19)
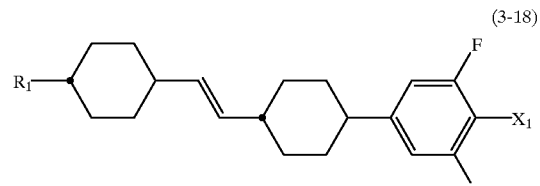
(3-20)
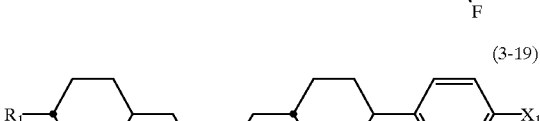
(3-21)
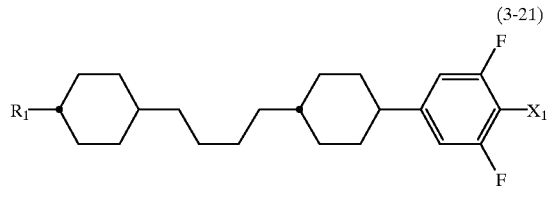
(3-22)
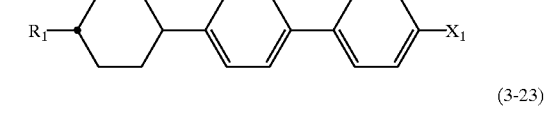
(3-23)
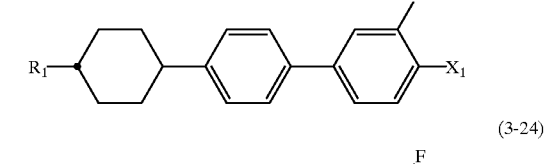
(3-24)
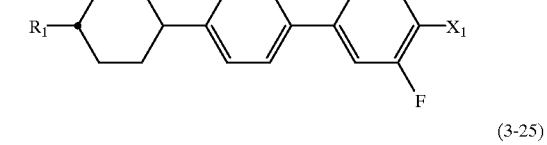
(3-25)
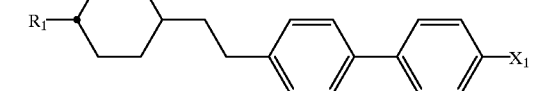
(3-26)
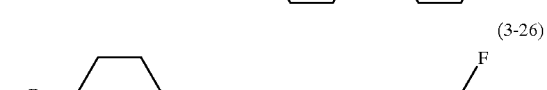
(3-27)
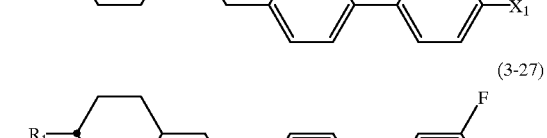
(3-28)
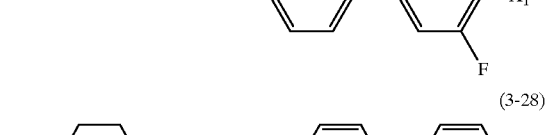
(3-29)
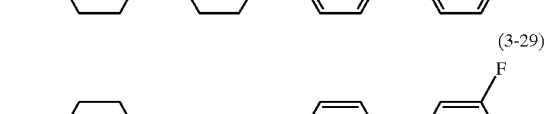
(3-30)
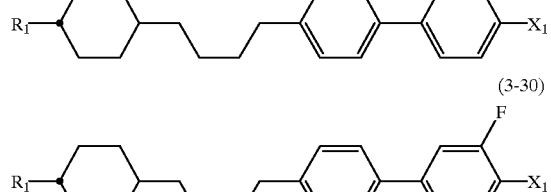

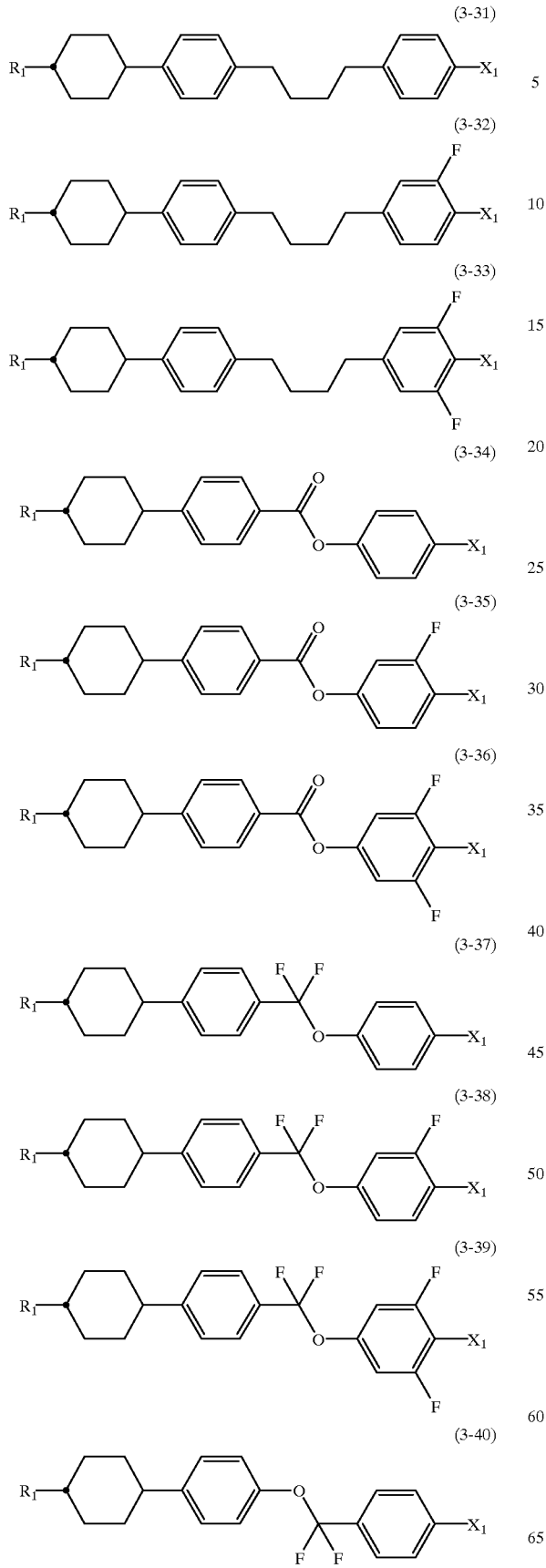
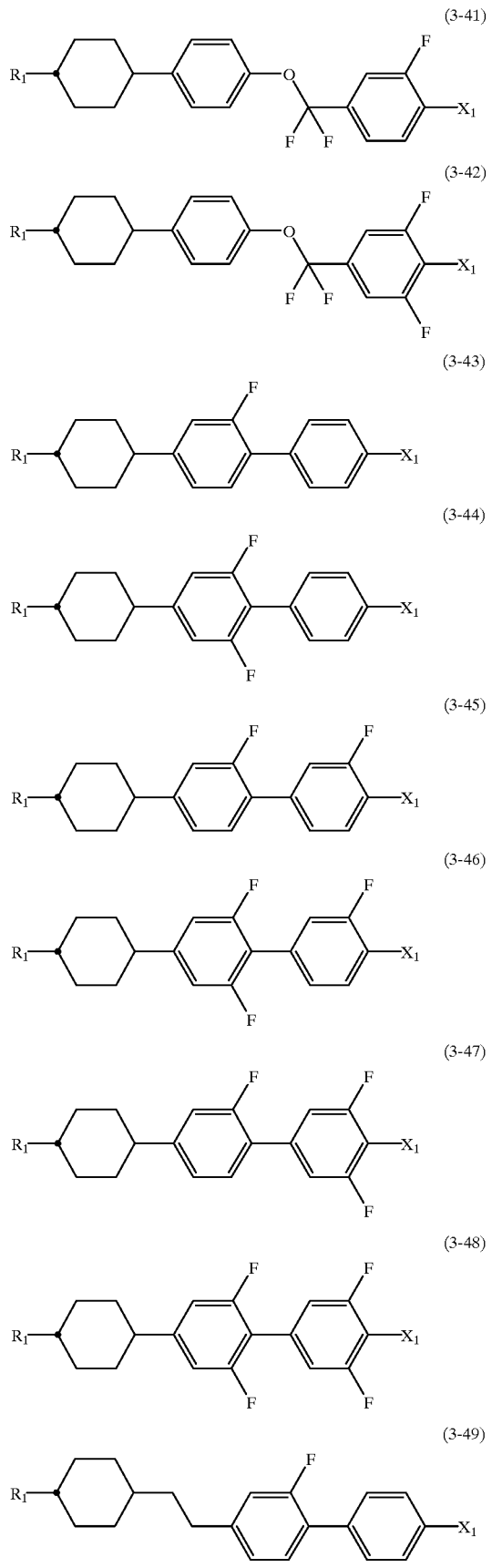

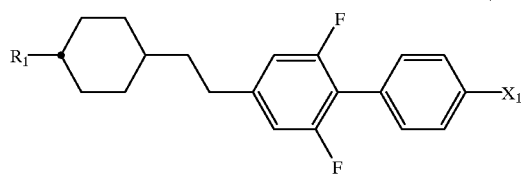
(3-50)
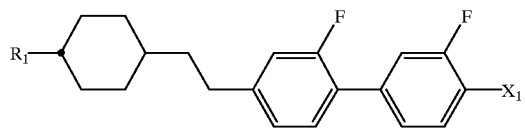
(3-51)
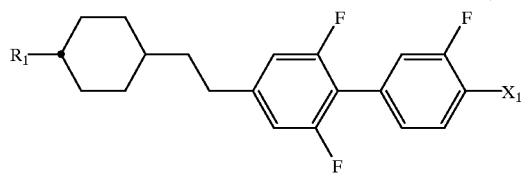
(3-52)
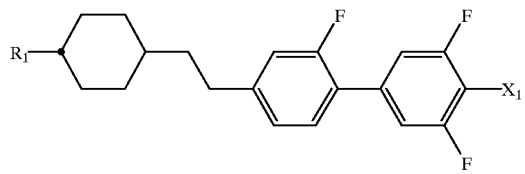
(3-53)
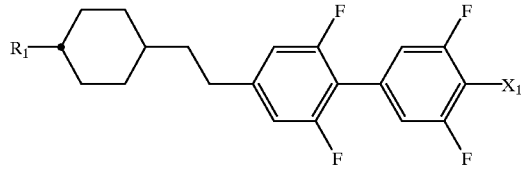
(3-54)
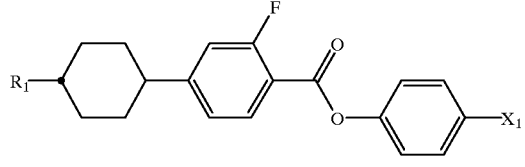
(3-55)
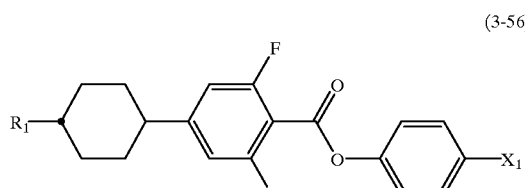
(3-56)
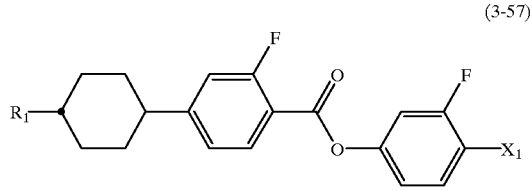
(3-57)
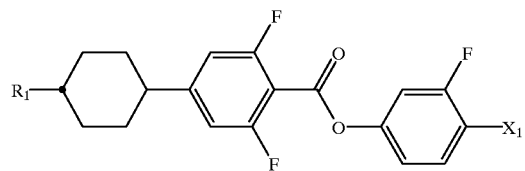
(3-58)
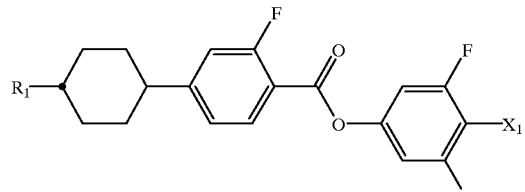
(3-59)
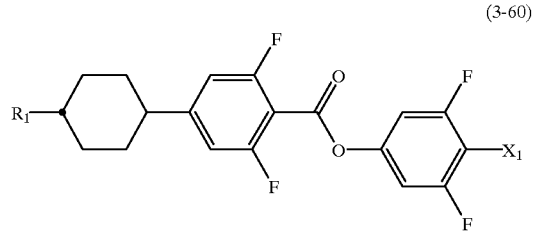
(3-60)
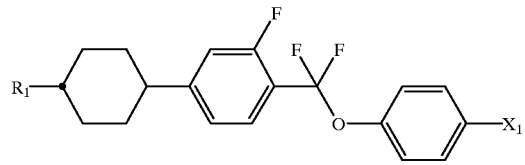
(3-61)
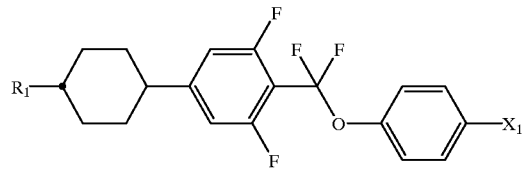
(3-62)
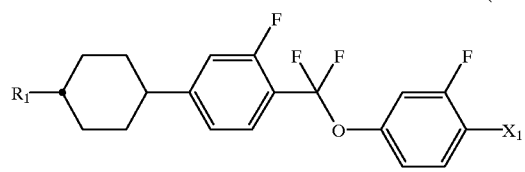
(3-63)
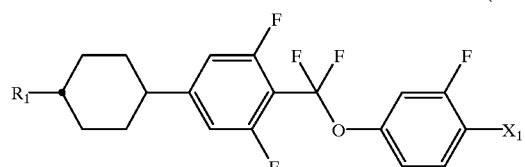
(3-64)

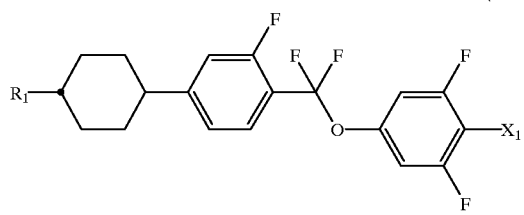
(3-65)
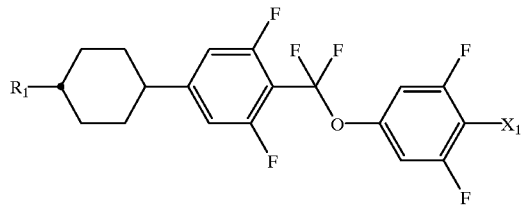
(3-66)
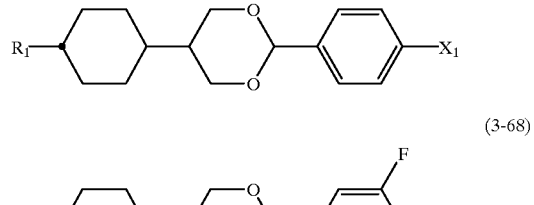
(3-67)
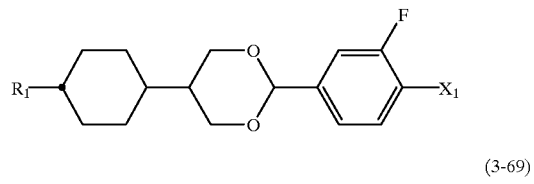
(3-68)
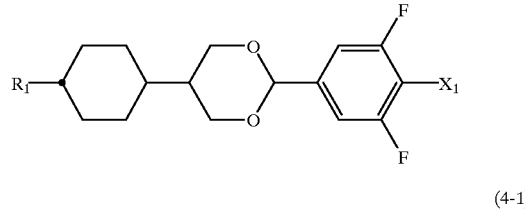
(3-69)
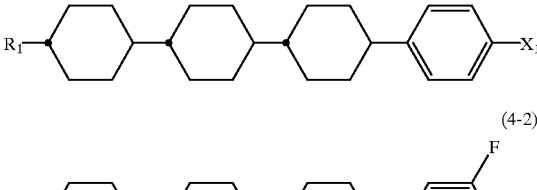
(4-1)
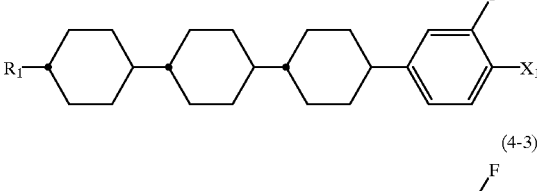
(4-2)
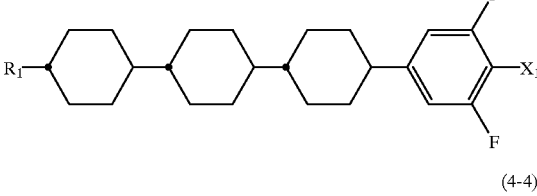
(4-3)
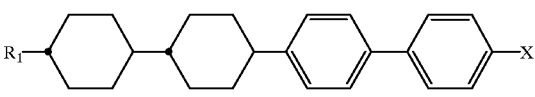
(4-4)
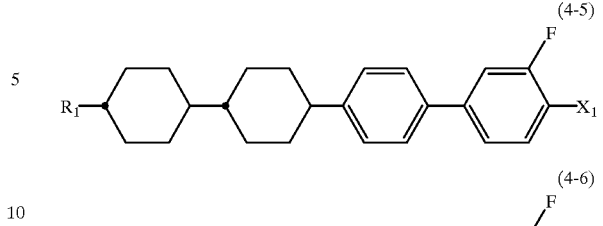
(4-5)
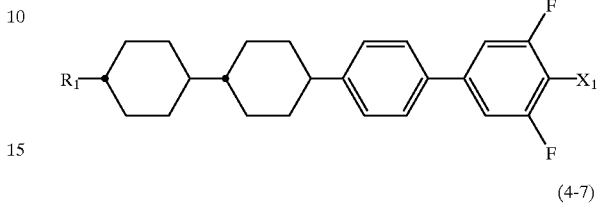
(4-6)
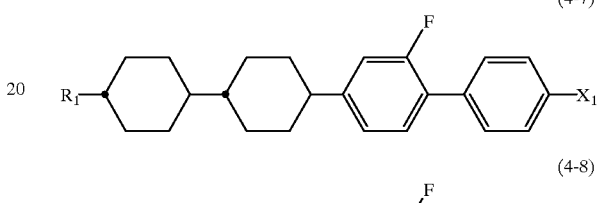
(4-7)
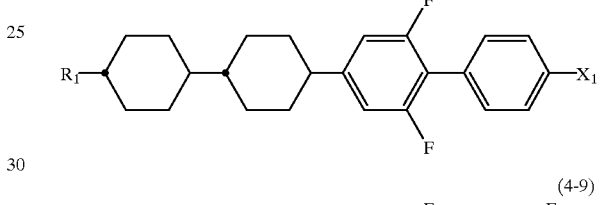
(4-8)
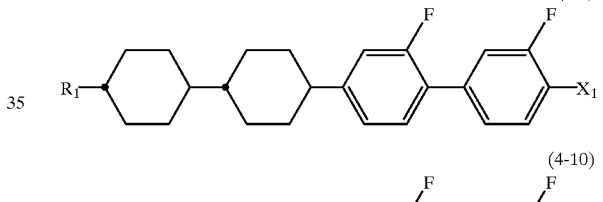
(4-9)
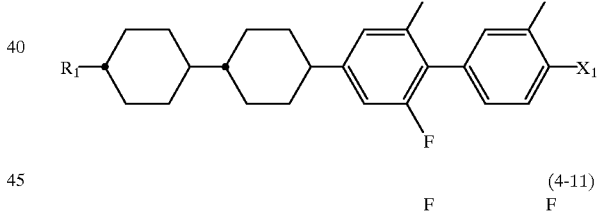
(4-10)
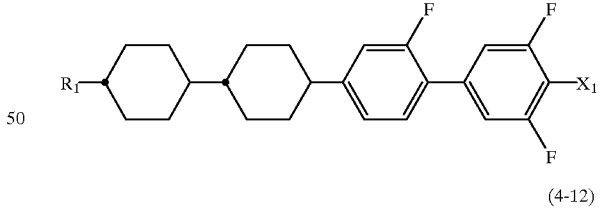
(4-11)
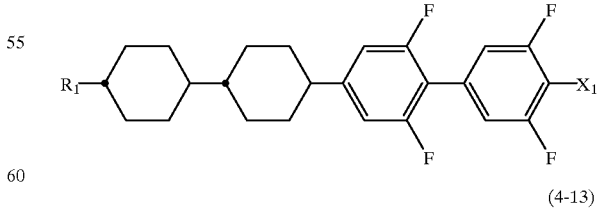
(4-12)
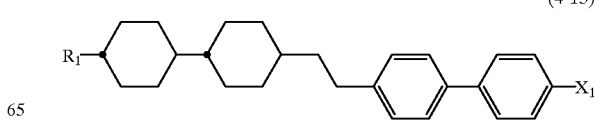
(4-13)

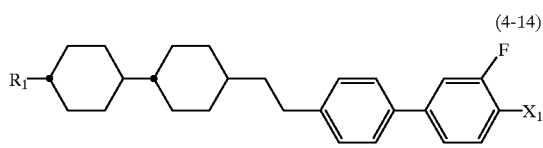
(4-14)

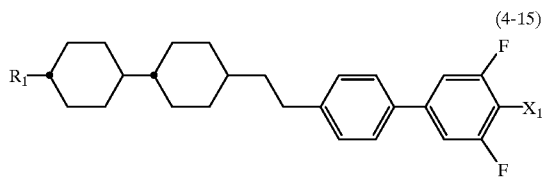
(4-15)

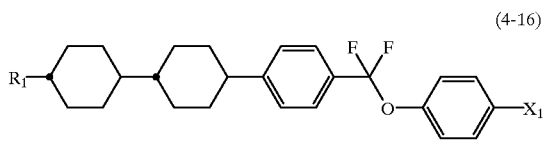
(4-16)

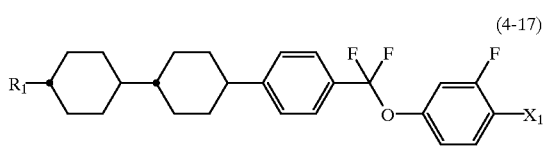
(4-17)

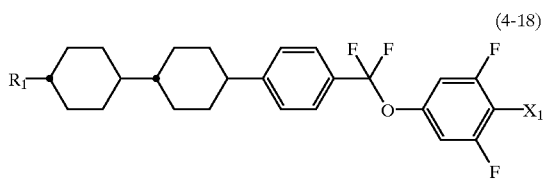
(4-18)

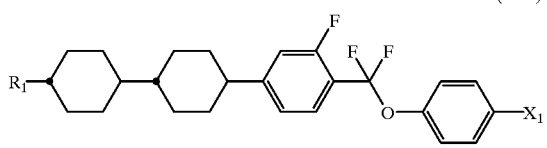
(4-19)

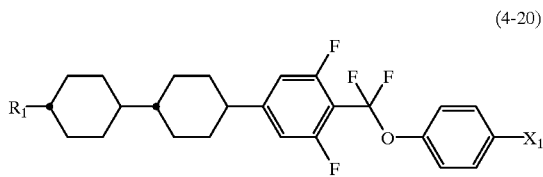
(4-20)

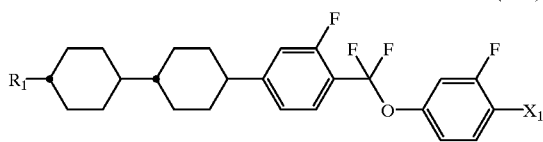
(4-21)

-continued

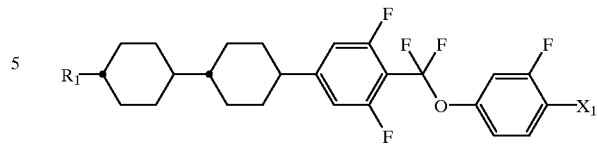
(4-22)

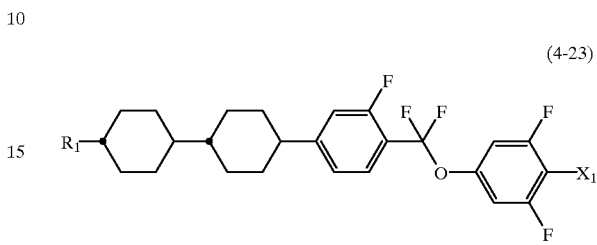
(4-23)

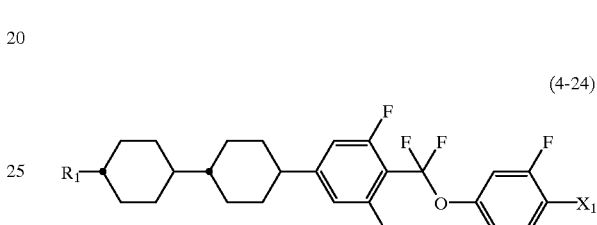
(4-24)

wherein $R_1$ and $X_1$ have the same meaning as described above.

Any of the compounds expressed by one of the general formulas (2) to (4) exhibit a positive $\Delta\epsilon$, are excellent in thermal stability and chemical stability, and are indispensable when liquid crystal compositions for TFT (AM-LCD) of which a high reliability such as a high voltage holding ratio (large specific resistivity) is required are produced.

While the amount of the compound to be used is suitably in the range of 1 to 99% by weight based on the total amount of liquid crystal composition when liquid crystal compositions for TFT are produced, it is preferably 10 to 97% by weight and more desirably 40 to 95% by weight. In this case, liquid crystal compositions may further comprise a compound expressed by one the general formulas (7) to (9) for the purpose of adjusting viscosity.

While the compounds expressed by one of the general formulas (2) to (4) described above can be used when liquid crystal compositions for STN display mode or TN display mode are produced, the amount of the compound to be used is preferably less than 50% by weight based on the total amount of liquid crystal composition since these compounds are small in their effect of lowering threshold voltage of liquid crystal compositions.

Next, among the second component B, the compounds of one the formulas (5-1) to (5-40) can be mentioned as preferable examples of the ones included in the general formula (5), and the compounds of one of the formulas (6-1) to (6-3) can be mentioned as preferable examples of the ones included in the general formula (6), respectively.

(5-1) 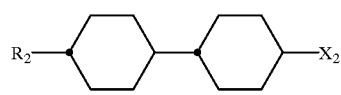
(5-2) 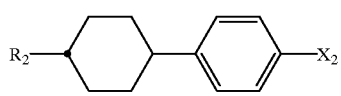
(5-3) 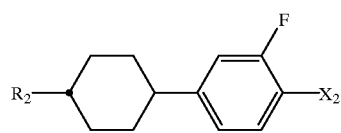
(5-4) 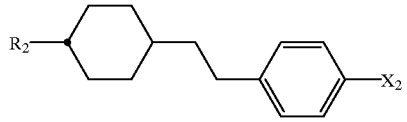
(5-5) 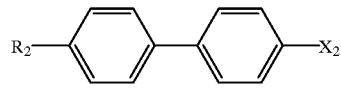
(5-6) 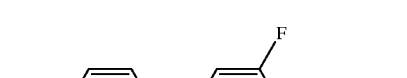
(5-7) 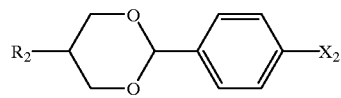
(5-8) 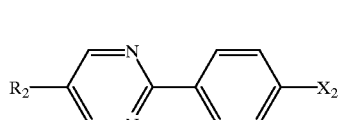
(5-9) 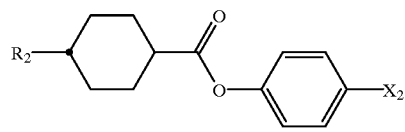
(5-10) 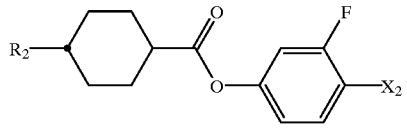
(5-11) 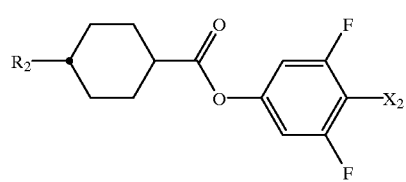
(5-12) 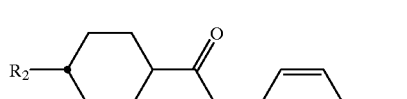
(5-13) 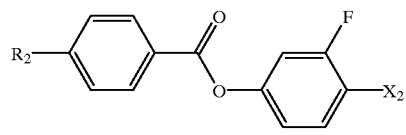
(5-14) 
(5-15) 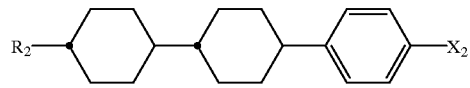
(5-16) 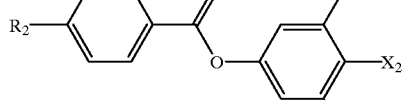
(5-17) 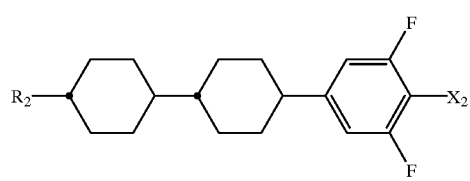
(5-18) 
(5-19) 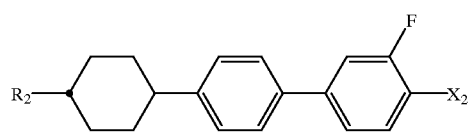
(5-20) 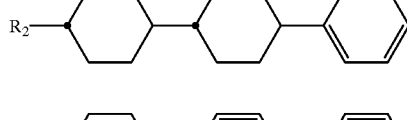

-continued
(5-21)
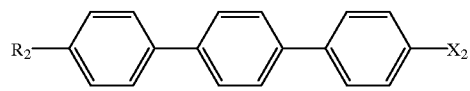
(5-22)
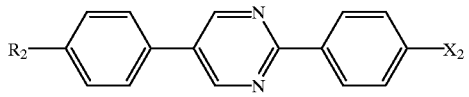
(5-23)
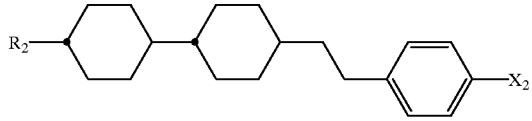
(5-24)
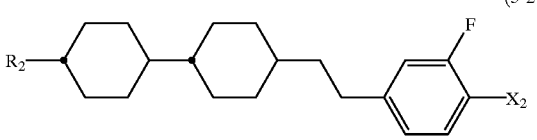
(5-25)
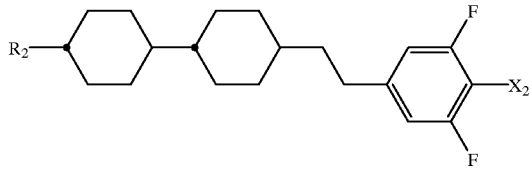
(5-26)
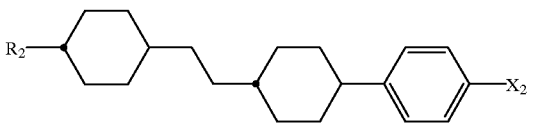
(5-27)
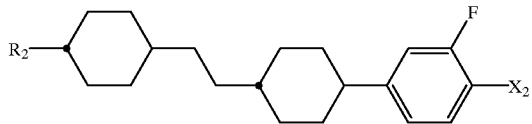
(5-28)
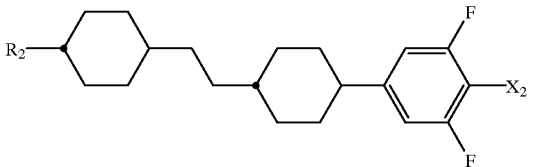
(5-29)
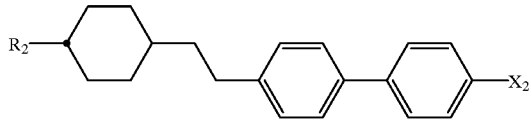
(5-30)
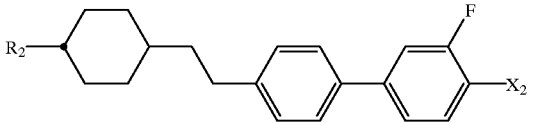
(5-31)
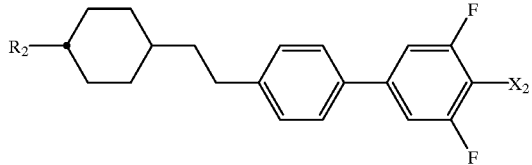
(5-32)
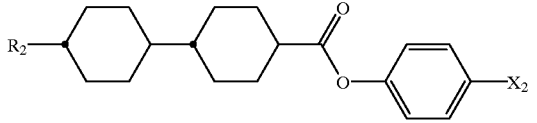
(5-33)
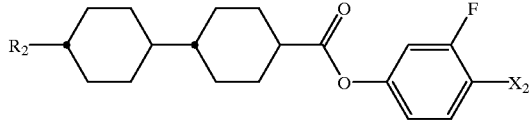
(5-34)
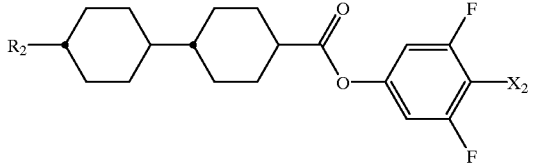
(5-35)
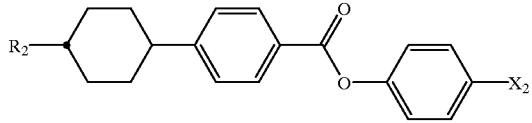
(5-36)
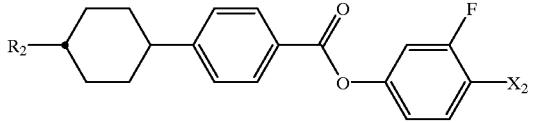
(5-37)
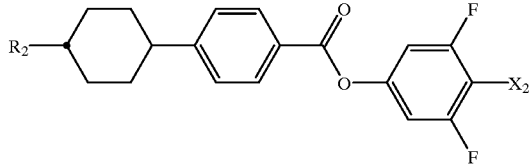
(5-38)
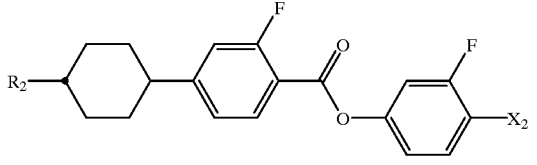

-continued

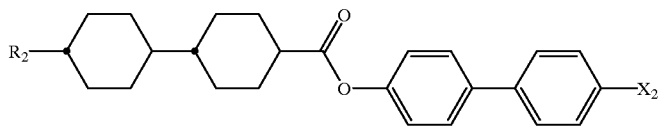
(5-39)

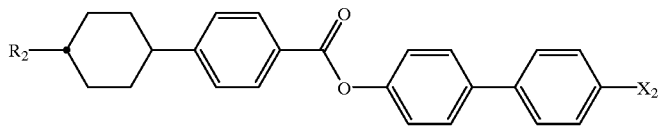
(5-40)

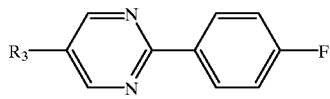
(6-1)

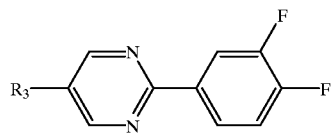
(6-2)

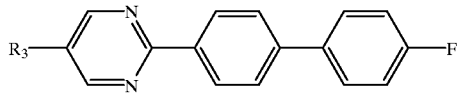
(6-3)

wherein $R_2$, $R_3$, and $X_2$ have the same meaning as described above.

Any compounds expressed by the general formula (5) or (6) have a positive and large $\Delta\epsilon$ value, and are used particularly for the purpose of lowering threshold voltage of liquid crystal compositions.

Also, the compounds are used for the purpose of improving the steepness of viscosity of liquid crystal compositions for STN display mode or TN display mode including for the purpose adjusting $\Delta n$ and widening temperature range of nematic phase such as raising clearing point of liquid crystal compositions, and thus are indispensable particularly when liquid crystal compositions for STN display mode or ordinary TN display mode are produced.

Whereas the compounds can lower threshold voltage of liquid crystal compositions as their amount used is increased, the use of the compounds bring about increase of the viscosity. Accordingly, it is advantageous to use the compounds in a large amount for driving devices at a low voltage so far as the viscosity of liquid crystal compositions satisfies required characteristics.

From such circumstances, the amount of the compounds to be used is suitably in the range of 0.1 to 99.9% by weight, preferably 10 to 97% by weight, and more desirably 40 to 95% by weight based on the total amount of liquid crystal composition when liquid crystal compositions for STN display mode or TN display mode are produced.

Among the third component described above, the compounds one of the following formulas (7-1) to (7-11) can be mentioned as preferable examples of the ones included in the general formula (7), the compounds of one of the formulas (8-1) to (8-18) can be mentioned as preferable examples of the ones included in the general formula (8), and the compounds of one of the formulas (9-1) to (9-6) as preferable examples of the compounds included in the general formula (9).

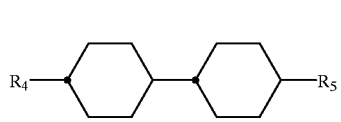
(7-1)

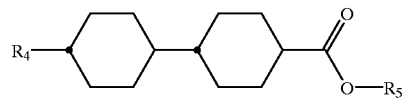
(7-2)

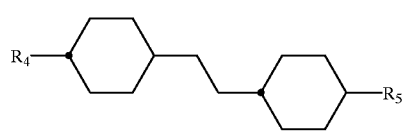
(7-3)

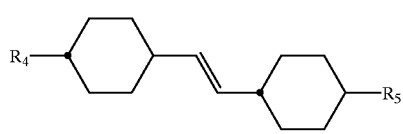
(7-4)

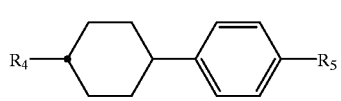
(7-5)

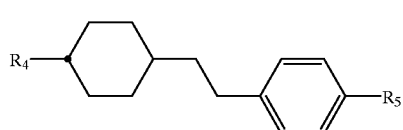
(7-6)

-continued
(7-7)
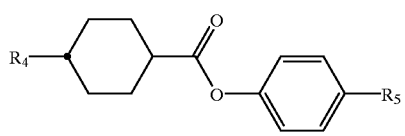
(7-8)
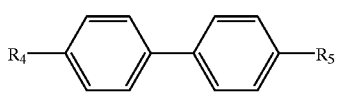
(7-9)
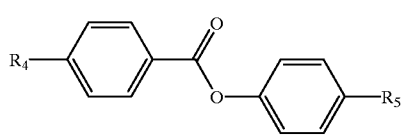
(7-10)
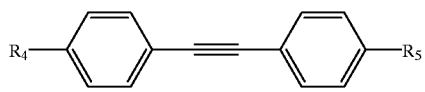
(7-11)
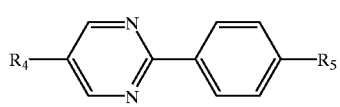
(8-1)
(8-2)
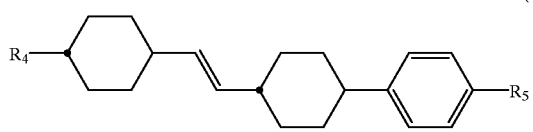
(8-3)
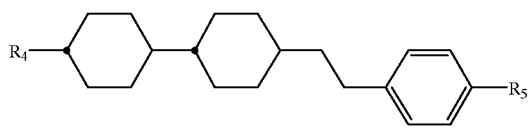
(8-4)
(8-5)
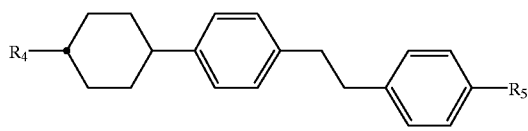
(8-6)
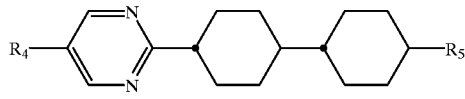
(8-7)
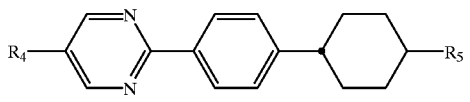
(8-8)
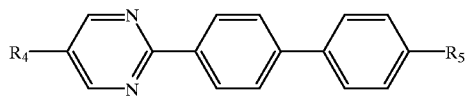
(8-9)
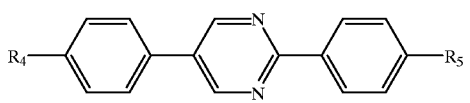
(8-10)
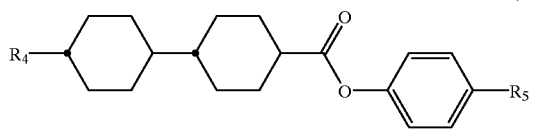
(8-11)
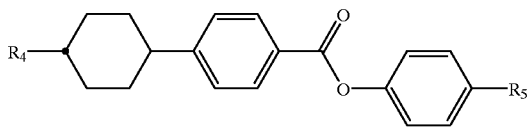
(8-12)
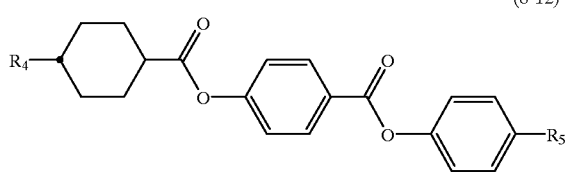
(8-13)
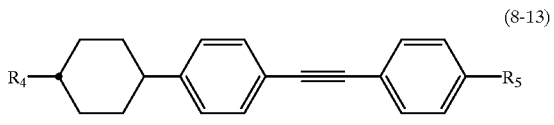
(8-14)
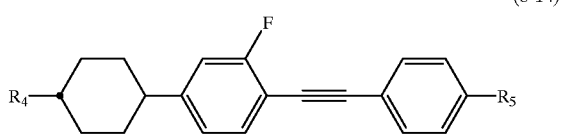
(8-15)
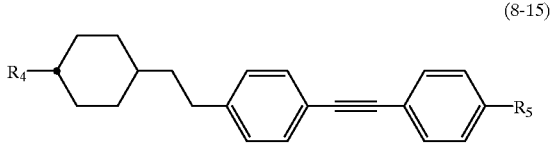

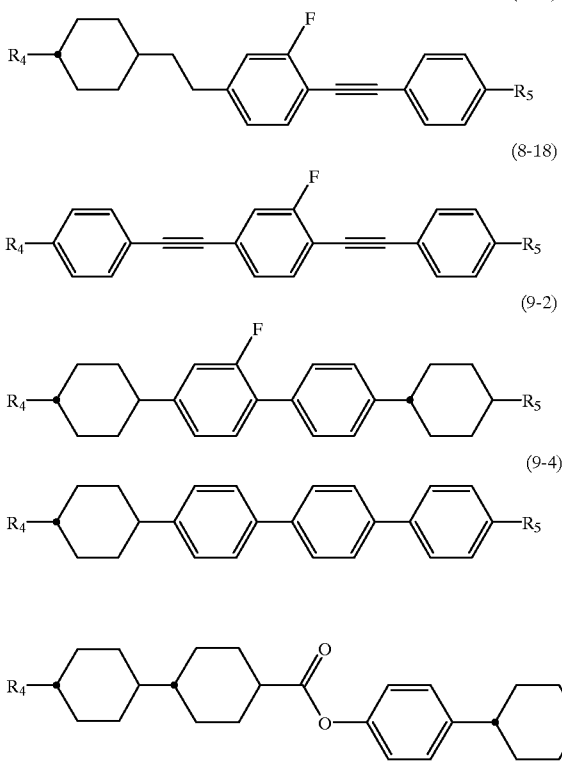

wherein $R_4$ and $R_5$ have the same meaning as described above.

Any compounds expressed by one of the general formulas (7) to (9) have a small absolute value of $\Delta\epsilon$. Among them, the compounds of the general formula (7) are used principally for the purpose of adjusting viscosity or adjusting $\Delta n$ of liquid crystal compositions, and the compounds of the general formula (8) or (9) are used for the purpose of widening nematic range and adjusting $\Delta n$.

Whereas these compounds raise threshold voltage of liquid crystal compositions as their amount used is increased, the use of the compounds reduces the viscosity. Accordingly, it is desirable to use the compounds in a larger amount so far as the threshold voltage of liquid crystal compositions satisfies required values.

From such circumstances, the amount of the compounds to be used is suitably less than 40% by weight and preferably less than 35% by weight based on the total amount of liquid crystal composition when liquid crystal compositions for TFT are produced. On the other hand, when liquid crystal composition for STN display mode or TN display mode are produced, the amount of use described above is preferably less than 70% by weight and preferably less than 60% by weight based on the total amount of liquid crystal composition.

Next, among other components, an optically active compound is usually added to the liquid crystal compositions of the present invention for the purpose of inducing helical structure of liquid crystal composition to adjust required twist angle and to prevent reverse twist, with the exception of specific cases, for instance, the case of liquid crystal compositions for OCB (Optically Compensated Birefringence) mode.

While the optically active compound is widely selected from known compounds so far as the purposes described above can be achieved, the optically active compound expressed by one of the following formulas (Op-1) to (Op-8) can preferably be mentioned:

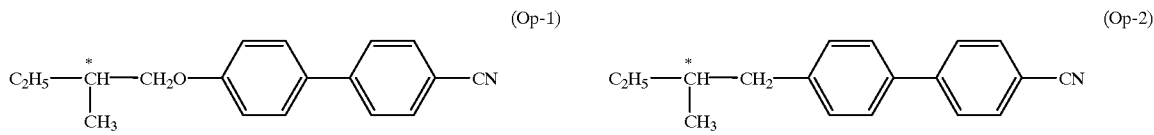

-continued

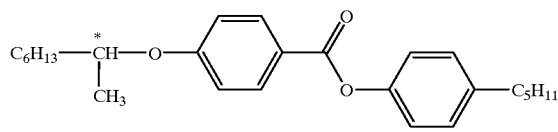
(Op-3)

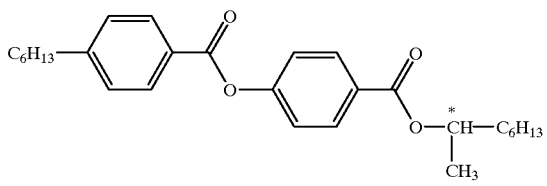
(Op-4)

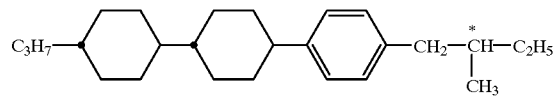
(Op-5)

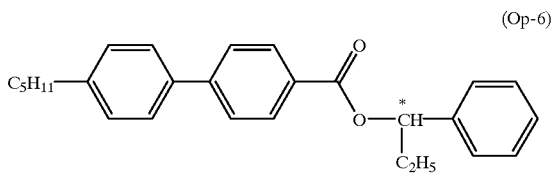
(Op-6)

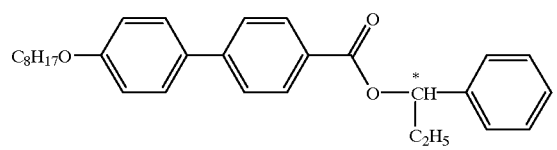
(Op-7)

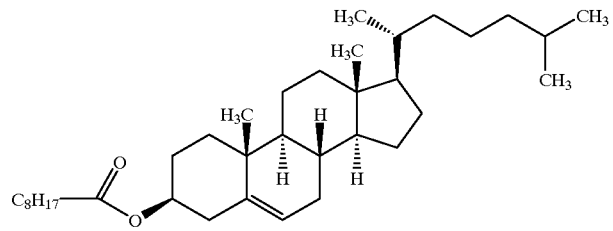
(Op-8)

Pitch length of the twist in liquid crystal compositions are adjusted by adding these optically active compounds. The twist pitch length is preferably adjusted in the range of 40 to 200 μm in the case of liquid crystal compositions for TFT or TN, preferably adjusted in the range of 6 to 20 μm in the case of the compositions for STN, and preferably adjusted in the range of 1.5 to 4 μm in the case of compositions for bistable TN mode, respectively. Further, in such cases, two or more kind of optically active compounds may be added for the purpose of adjusting the dependency of pitch length on temperature.

Liquid crystal compositions of the present invention can be produced by methods which are conventional by themselves. For instance, the compositions are produced by a method in which various components are dissolved in one another at a high temperature, or a method in which various components are dissolved in an organic solvent to mix and then the solvent is distilled off under a reduced pressure.

Further, the liquid crystal compositions of the present invention can be used as ones for guest-host (GH) mode by adding a dichroic dye such as merocyanine type, styryl type, azo type azomethine type, azoxy type, quinophthalone type, anthraquinone type, and tetrazine type thereto. Alternatively, the liquid crystal compositions can be used as NCAP which is prepared by the microencapsulation of a nematic liquid crystal, or as liquid crystal compositions for polymer dispersed liquid crystal display devices (PDLCD) represented by polymer net work liquid crystal display devices (PNLCD) prepared by forming a polymer of three-dimensional reticulated structure in a liquid crystal. Still further, the liquid crystal compositions of the present invention can be used as ones for electrically controlled birefringence (ECB) mode or dynamic scattering (DS) mode.

Compounds of the present invention expressed by the general formula (1) can be produced by known methods of ordinary organic synthesis.

Production of compounds expressed by the general formula (1) in which M=COOH:

Conjugated aldehyde expressed by the formula (14) is obtained by reacting the compound expressed by the formula (12) with phosphorane which is prepared from 1,3-dioxane-2-ylethyltriphenylphosphonium bromide and a base, to convert into exo-olefin compound (13), and then treating it with an acid. Compound of the present invention expressed by the general formula (1) is obtained by oxidizing an aldehyde of the formula (14) with an oxidizing agent such as silver oxide.

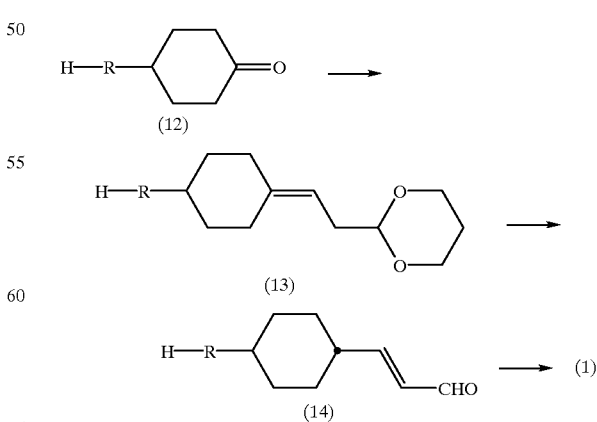

wherein R has the same meaning as described above.

Production of compounds expressed by the general formula (1) in which M=CN:

Compounds of the present invention expressed by the general formula (1) can be obtained by reacting a compound of the formula (15), which is known as starting raw material for liquid crystal materials, with a metal cyanide in an aprotic polar solvent.

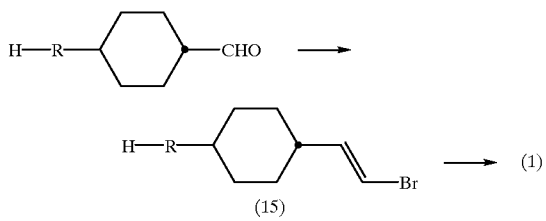

wherein R has the same meaning as described above.

Now, the present invention will be described in more detail with reference to Examples. However, it should be understood that the scope of the present invention is by no means restricted by such specific Examples.

In each of the Examples, C indicates crystal, N: nematic phase, and I: isotropic liquid phase, and the unit of all phase transition temperatures is ° C.

EXAMPLE 1

Preparation of 3-(trans-4-pentylcyclohexyl)acrylic acid (Compound No. 4)

To 300 ml of tetrahydrofuran was dissolved 55 g of 1,3-dioxane-2-ylethyltriphenylphosphonium bromide, 14.5 g of potassium-t-butoxide was added thereto while being stirred and cooled with ice, and then the solution was stirred for further 30 minutes. To this reaction liquid was added by drops 50 ml of a solution prepared by dissolving 16.8 g of 4-pentylcyclohexanone in 50 ml of tetrahydrofuran, and the solution was stirred under cooling with ice for 2 hours and then stirred at room temperature for 3 hours. After termination of the reaction, the solution was filtered by using a silica gel short column chromatography and concentrated under a reduced pressure. The brown oily product thus obtained was isolated purified by silica gel column chromatography to obtain 15.2 g a colorless oily product. As a result of various instrumental analyses, the product was confirmed to be 4-pentyl-1-(1,3-dioxane-2-ylethylidene)cyclohexane.

This compound in an amount of 15.2 g and 5 ml of 2N hydrochloric acid were dissolved in 150 ml of acetone, and stirred under reflux by heating for 3 hours. The reaction solution was cooled and then extracted with ether. The organic layer thus obtained was washed with water, dried, and then concentrated under a reduced pressure to obtain 10 g of 3-(trans-4-propylcyclohexyl)-2-propenal. This product was used for subsequent reaction without purification.

A solution of 6 g of sodium hydroxide in 150 ml of water-methanol was gradually added by drops to a suspension of 34 g of silver oxide in water at room temperature while being stirred, 10 of the compound obtained by the procedure described above was added without purification to this reaction system, and they were stirred at 40° C. for 2 hours. After finishing of the stirring, the solution was filtered under a reduced pressure remove undissolved substances, and then extracted with methyl chloride. The organic layer was washed with water, dried, and then concentrated under a reduced pressure to obtain a pale yellow solid. This solid was recrystallized from methylene chloride to obtain 4 g of colorless solid.

As a result of various instrumental analysises, the product was confirmed to be the subject compound.

C.91.6 N.168.8 I

Rough LD50 value (medium lethal dose caused by acute toxity through single oral administration) of this compound was determined by orally administering the compound (specimen) to a group of mice as a single oral dose and observing for 14 days be more than 3000 mg/kg, and thus the compound was presumed to be extremely low toxic.

EXAMPLE 2

Preparation of 3-(trans-4-propylcyclohexyl) acrylonitrile (Compound No. 12)

To 30 ml of N-methylpyrrolidone was dissolved 3 g of 2-(trans-4-propylcyclohexyl)ethenyl bromide, 2 g of copper cyanide was added thereto, and then stirred under reflux by heating for 7 hours. A solution of ferric chloride in 6N hydrochloric acid was added to the reaction liquid, and extracted with toluene. The organic layer thus obtained was washed with water, dried, and then concentrated under a reduced pressure to obtain a brown oily product. This product was isolated and purified by using silica gel column chromatography to obtain 1.5 g of an oily product. As a result of various instrumental analysises, the product was confirmed to be the subject compound.

Based on the descriptions in Example 1 and Example 2, the following compounds, Compound No. 1 through No. 20 can be prepared.

In the following, compounds obtained in Example 1 and Example 2 are shown again.

| No. | H—R | M |
| --- | --- | --- |
| 1 | $CH_3CH_2$ | —COOH |
| 2 | $CH_3CH_2CH_2$ | —COOH |
| 3 | $CH_3(CH_2)_3$ | —COOH |
| 4 | $CH_3(CH_2)_4$ | —COOH |
| 5 | $CH_3(CH_2)_6$ | —COOH |
| 6 | $CH_2=CH$ | —COOH |
| 7 | $CH_2=CH—CH_2CH_2$ | —COOH |
| 8 | $CH_3CH_2=CHCH_2CH_2$ | —COOH |
| 9 | $CH_3OCH_2$ | —COOH |
| 10 | $CH_3CH_2CH_2OCH_2$ | —COOH |
| 11 | $CH_3CH_2$ | —CN |
| 12 | $CH_3CH_2CH_2$ | —CN |
| 13 | $CH_3(CH_2)_3$ | —CN |
| 14 | $CH_3(CH_2)_4$ | —CN |
| 15 | $CH_3(CH_2)_6$ | —CN |
| 16 | $CH_2=CH$ | —CN |
| 17 | $CH_2=CH—CH_2CH_2$ | —CN |
| 18 | $CH_3CH_2=CHCH_2CH_2$ | —CN |
| 19 | $CH_3OCH_2$ | —CN |
| 20 | $CH_3CH_2CH_2OCH_2$ | —CN |

Examples of liquid crystal compositions comprising the compound of the present invention are shown as Examples below.

In each of the following Composition Examples, compounds are designated by making the groups shown in each of columns of left side terminal group, bonding group, ring structure, and right side terminal group correspond to the symbols shown in the columns of symbol according to the definition shown in Table 1 below. When the hydrogen atom on trans-1,4-cyclohexylene group or trans-bicyclohexane-4,4'-diyl group is replaced by heavy hydrogen atom (deuterium) of isotope, it is designated by symbol [1D,~8D] by assuming that any of hydrogen atoms $L^1, L^2, L^3, L^4, L^5,$ $L^6$, $L^7$, and $L^8$ on the ring is replaced by corresponding heavy hydrogen atom selected from heavy hydrogen atoms 1D, 2D, 3D, 4D, 5D, 6D, 7D, and 8D in turn when each of the groups mentioned above is expressed by the formula (60) or (61), and excerpting only heavy hydrogen atom after replacement.

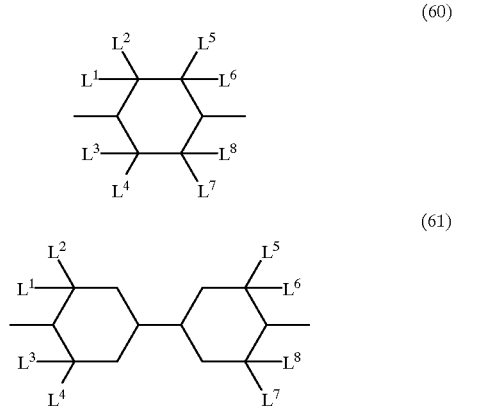

Compound No. appended to the compounds of the present invention in the following Composition Examples means that the compounds are the same as those shown in Examples described below and having the same appended Compound No.; and the content of compounds means % by weight unless otherwise specified.

Further, data of characteristics of compositions in Composition Examples are indicated by $T_{NI}$ (phase transition temperature of nematic phase-isotropic liquid, or clearing point), $\eta$ (viscosity: determined at 20.0° C.), $\Delta n$ (optical anisotropy value: determined at 25.0° C.), $\Delta\epsilon$ (dielectric anisotropy value: determined at 25.0° C.), $V_{th}$ (threshold voltage: determined at 25.0° C.), and P (pitch: determined at 25.0° C.).

TABLE 1

R—($A_1$)—$Z_1$— . . . —$Z_n$—($A_n$)—X

| 1) Left side terminal group R— | Symbol |
|---|---|
| $C_nH_{2n+1}$— | n- |
| $C_nH_{2n+1}O$— | nO- |
| $C_nH_{2n+1}OC_mH_{2m}$— | nOm- |
| $CH_2$=CH— | V— |
| $CH_2$=CH$C_nH_{2n}$— | Vn- |
| $C_nH_{2n+1}CH$=CH$C_mH_{2m}$— | nVm- |
| $C_nH_{2n+1}CH$=CH$C_mH_{2m}CH$=CH$C_kH_{2k}$— | nVmVk- |

| 2) Ring structure —($A_1$)—, —($A_n$)— | Symbol |
|---|---|
| (benzene) | B |
| (fluorobenzene) | B(F) |
| (2,3-difluorobenzene) | B(2F,3F) |
| (trifluorobenzene) | B(F,F) |
| (cyclohexane) | H |
| (pyrimidine) | Py |
| (dioxane) | G |
| (cyclohexene) | Ch |

| 3) Bonding group —$Z_1$—, —$Z_n$— | Symbol |
|---|---|
| —$C_2H_4$— | 2 |
| —$C_4H_8$— | 4 |
| —COO— | E |
| —C≡C— | T |
| —CH=CH— | V |
| —$CF_2O$— | CF2O |
| —$OCF_2$— | OCF2 |

| 4) Right side terminal group —X | Symbol |
|---|---|
| —F | —F |
| —Cl | —CL |
| —CN | —C |
| —$CF_3$ | —CF3 |
| —$OCF_3$ | —OCF3 |
| —$OCF_2H$ | —OCF2H |
| —$C_nH_{2n+1}$ | -n |
| —$OC_nH_{2n+1}$ | —On |
| —$COOCH_3$ | —EMe |
| —$C_nH_{2n}CH$=$CH_2$ | -nV |
| —$C_mH_{2m}CH$=$CHC_nH_{2n+1}$ | -mVn |
| —$C_mH_{2m}CH$=$CHC_nH_{2n}F$ | -mVnF |
| —CH=$CF_2$ | —VFF |
| —$C_nH_{2n}CH$=$CF_2$ | -nVFF |
| —C≡C—CN | —TC |
| —CH=CH—COOH | —VCOOH |
| —CH=CH—CN | —VC |

5) Example of designation

Example 1
3-H2B(F,F)B(F)—F

TABLE 1-continued

R—(A₁)—Z₁— ... —Zₙ—(Aₙ)—X

Example 2
3-HB(F)TB—2

Example 3
1V2-BEB(F,F)—C

EXAMPLE 3

Composition Example 1

Liquid crystal composition comprising the following compounds in the amount shown below was prepared:

| | | |
|---|---|---|
| 5-H—VCOOH | (No. 4) | 15.0% |
| 3-HB—C | | 20.0% |
| 5-HB—C | | 31.0% |
| 7-HB—C | | 21.0% |
| 5-HBB—C | | 13.0% |

Characteristics of this composition were determined to be follows:

$T_{NI}$=92.2° C.
$\eta$=32.1 mPa.s
$\Delta n$=0.1350
$\Delta \epsilon$=9.70
$V_{th}$=1.94 V (cell thickness: 9.3 μm)

EXAMPLE 4

Composition Example 2

Liquid crystal composition comprising the following compounds in the amount shown below was prepared:

| | | |
|---|---|---|
| 3-H—VCOOH | (No. 2) | 15.0% |
| 3-HB—C | | 20.0% |
| 5-HB—C | | 31.0% |
| 7-HB—C | | 21.0% |
| 5-HBB—C | | 13.0% |

Characteristics of this composition were determined to be as follows:

$T_{NI}$=92.6° C.
$\eta$=29.0 mPa.s
$\Delta n$=0.1370
$\Delta \epsilon$=9.90
$V_{th}$=1.84 V (cell thickness: 9.2 μm)

EXAMPLE 5

Composition Example 3

Liquid crystal composition comprising the following compounds in the amount shown below was prepared:

| | | |
|---|---|---|
| 3-H—VC | (No. 12) | 15.0% |
| 3-HB—C | | 20.0% |
| 5-HB—C | | 31.0% |
| 7-HB—C | | 21.0% |
| 5-HBB—C | | 13.0% |

Characteristics of this composition were determined to be as follows:

$T_{NI}$=49.3° C.
$\eta$=21.0 mPa.s
$\Delta n$=0.1260
$\Delta \epsilon$=10.2
$V_{th}$=1.31 V (cell thickness: 9.3 μm)

EXAMPLE 6

Composition Example 4

Liquid crystal composition comprising the following compounds in the amount shown below was prepared:

| | | |
|---|---|---|
| 3-H—VCOOH | (No. 2) | 6.0% |
| 5-H—VCOOH | (No. 4) | 6.0% |
| 2O1-BEB(F)—C | | 5.0% |
| 3O1-BEB(F)—C | | 15.0% |
| 4O1-BEB(F)—C | | 13.0% |
| 5O1-BEB(F)—C | | 13.0% |
| 2-HHB(F)—C | | 15.0% |
| 3-HHB(F)—C | | 15.0% |
| 3-HB(F)TB-2 | | 4.0% |
| 3-HB(F)TB-3 | | 3.0% |
| 3-HB(F)TB-4 | | 3.0% |
| 3-HHB-1 | | 2.0% |

Characteristics of this composition were determined to be as follows:

$T_{NI}$=93.7° C.
$\eta$=88.8 mPa.s
$\Delta n$=0.148
$\Delta \epsilon$=31.3
$V_{th}$=0.87 V (cell thickness: 9.3 μm)

EXAMPLE 7

Composition Example 5

Liquid crystal composition comprising the following compounds in the amount shown below was prepared:

| | | |
|---|---|---|
| 3-H—VCOOH | (No. 2) | 5.0% |
| 5-H—VCOOH | (No. 4) | 4.0% |
| 1V2-BEB(F,F)—C | | 5.0% |
| 3-HB—C | | 25.0% |
| 1-BTB-3 | | 5.0% |
| 2-BTB-1 | | 10.0% |
| 3-HH-4 | | 11.0% |
| 3-HHB-1 | | 11.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 6.0% |

Characteristics of this composition were determined to be as follows:

$T_{NI}$=94.1° C.

$\eta$=15.0 mPa.s $\Delta n$=0.163

$\Delta \epsilon$=7.1

$V_{th}$=2.12 V

Optically active compound expressed by the formula (Op-4) described above in an amount of 0.8 part by weight was added to 100 parts by weight of the primary composition described just above to obtain a secondary composition, and characteristic of the secondary composition was determined to be as follows:

P=10.8 μm

EXAMPLE 8

Composition Example 6

Liquid crystal composition comprising the following compounds in the amount shown below was prepared:

| | | |
|---|---|---|
| 3-H—VCOOH | (No. 2) | 5.0% |
| V2-HB—C | | 12.0% |
| 1V2-HB—C | | 12.0% |
| 3-HB—C | | 15.0% |
| 3-H[1D,2D,3D]—C | | 9.0% |
| 3-HB(F)—C | | 5.0% |
| 2-BTB-1 | | 2.0% |
| 3-HH-4 | | 8.0% |
| 3-HH—VFF | | 6.0% |
| 2-H[1D,2D,3D]HB—C | | 3.0% |
| 3-HHB—C | | 6.0% |
| 3-HB(F)TB-2 | | 3.0% |
| 3-H2BTB-2 | | 5.0% |
| 3-H2BTB-3 | | 5.0% |
| 3-H2BTB-4 | | 4.0% |

Characteristics of this composition were determined to be as follows:

$T_{NI}$=89.2° C.

$\eta$=17.9 mPa.s $\Delta n$=0.148

$\Delta \epsilon$=8.7

$V_{th}$=2.01 V

EXAMPLE 9

Composition Example 7

Liquid crystal composition comprising the following compounds in the amount shown below was prepared:

| | | |
|---|---|---|
| 3-H—VCOOH | (No. 2) | 13.0% |
| 5-H—VCOOH | (No. 4) | 12.0% |
| 3-H—VC | (No. 12) | 5.0% |
| 3-HB—C | | 18.0% |
| 7-HB—C | | 3.0% |
| 1O1-HB—C | | 10.0% |
| 3-HB(F)—C | | 10.0% |
| 2-PyB-2 | | 2.0% |
| 3-PyB-2 | | 2.0% |
| 4-PyB-2 | | 2.0% |
| 1O1-HH-3 | | 2.0% |
| 2-BTB—O1 | | 7.0% |
| 3-HHB—F | | 4.0% |
| 3-H2BTB-2 | | 3.0% |
| 2-PyBH-3 | | 4.0% |
| 3-PyBB-2 | | 3.0% |

Characteristics of this composition were determined to be as follows:

$T_{NI}$=80.6° C.

$\eta$=18.8 mPa.s $\Delta n$=0.133

$\Delta \epsilon$=8.5

$V_{th}$=1.69 V

EXAMPLE 10

Composition Example 8

Liquid crystal composition comprising the following compounds in the amount shown below was prepared:

| | | |
|---|---|---|
| 5-H—VCOOH | (No. 4) | 6.0% |
| 3-GB—C | | 10.0% |
| 4-GB—C | | 10.0% |
| 2-BEB—C | | 12.0% |
| 3-BEB—C | | 4.0% |
| 3-PyB(F)—F | | 6.0% |
| 3-HEB—O4 | | 8.0% |
| 4-HEB—O2 | | 6.0% |
| 5-HEB—O1 | | 6.0% |
| 3-HEB—O2 | | 5.0% |
| 5-HEB—O2 | | 4.0% |
| 5-HEB-5 | | 5.0% |
| 4-HEB-5 | | 4.0% |
| 1O—BEB-2 | | 4.0% |
| 3-HHB-1 | | 2.0% |
| 3-HHEBB—C | | 2.0% |
| 3-HBEBB—C | | 3.0% |
| 5-HBEBB—C | | 3.0% |

Characteristics of this composition were determined to be as follows:

$T_{NI}$=70.8° C.

$\eta$=38.9 mPa.s $\Delta n$=0.120

$\Delta \epsilon$=11.3

$V_{th}$=1.32 V

EXAMPLE 11

Composition Example 9

Liquid crystal composition comprising the following compounds in the amount shown below was prepared:

| | | |
|---|---|---|
| 3-H—VCOOH | (No. 2) | 6.0% |
| 5-H—VCOOH | (No. 4) | 6.0% |
| 3-H—VC | (No. 12) | 3.0% |
| 5-PyB—F | | 4.0% |
| 3-PyB(F)—F | | 3.0% |
| 2-BB—C | | 5.0% |
| 4-BB—C | | 4.0% |
| 5-BB—C | | 5.0% |
| 2-PyB-2 | | 2.0% |
| 3-PyB-2 | | 2.0% |
| 6-PyB—O5 | | 3.0% |
| 6-PyB—O6 | | 3.0% |
| 6-PyB—O7 | | 3.0% |
| 6-PyB—O8 | | 3.0% |
| 3-PyBB—F | | 6.0% |
| 4-PyBB—F | | 6.0% |
| 5-PyBB—F | | 6.0% |
| 3-HHB-1 | | 2.0% |
| 2-H2BTB-2 | | 4.0% |
| 2-H2BTB-3 | | 4.0% |
| 2-H2BTB-4 | | 5.0% |
| 3-H2BTB-2 | | 5.0% |
| 3-H2BTB-3 | | 5.0% |
| 3-H2BTB-4 | | 5.0% |

Characteristics of this composition were determined to be as follows:

$T_{NI}$=95.1° C.

η=34.4 mPa.s

Δn=0.199

Δε=6.7

$V_{th}$=2.23 V

EXAMPLE 12

Composition Example 10

Liquid crystal composition comprising the following compounds in the amount shown below was prepared:

| | | |
|---|---|---|
| 3-H—VCOOH | (No. 2) | 5.0% |
| 5-H—VCOOH | (No. 4) | 5.0% |
| 2O1-BEB(F)—C | | 5.0% |
| 3O1-BEB(F)—C | | 12.0% |
| 5O1-BEB(F)—C | | 4.0% |
| 1V2-BEB(F,F)—C | | 10.0% |
| 3-HH—EMe | | 10.0% |
| 3-HB—O2 | | 18.0% |
| 7-HEB—F | | 2.0% |
| 3-HHEB—F | | 2.0% |
| 5-HHEB—F | | 2.0% |
| 3-HBEB—F | | 4.0% |
| 2O1-HBEB(F)—C | | 2.0% |
| 3-HB(F)EB(F)—C | | 2.0% |
| 3-HBEB(F,F)—C | | 2.0% |
| 3-HHB—F | | 4.0% |
| 3-HHB—O1 | | 4.0% |
| 3-HHB-3 | | 3.0% |
| 3-HEBEB—F | | 2.0% |
| 3-HEBEB-1 | | 2.0% |

Characteristics of this composition were determined to be as follows:

$T_{NI}$=80.0° C.

η=37.0 mPa.s

Δn=0.115

Δε=23.7

$V_{th}$=1.00 V

EXAMPLE 13

Composition Example 11

Liquid crystal composition comprising the following compounds in the amount shown below was prepared:

| | | |
|---|---|---|
| 3-H—VCOOH | (No. 2) | 10.0% |
| 5-BEB(F)—C | | 5.0% |
| V—HB—C | | 11.0% |
| 5-PyB—C | | 6.0% |
| 4-BB-3 | | 11.0% |
| 3-HH-2V | | 10.0% |
| 5-HH—V | | 11.0% |
| V—HHB-1 | | 7.0% |
| V2-HHB-1 | | 12.0% |
| 3-HHB-1 | | 2.0% |
| 1V2-HBB-2 | | 10.0% |
| 3-HHEBH-3 | | 5.0% |

Characteristics of this composition were determined to be as follows:

$T_{NI}$=93.7° C.

η=16.1 mPa.s

Δn=0.116

Δε=4.8

$V_{th}$=2.38 V

EXAMPLE 14

Composition Example 12

Liquid crystal composition comprising the following compounds in the amount shown below was prepared:

| | | |
|---|---|---|
| 5-H—VCOOH | (No. 4) | 8.0% |
| 2O1-BEB(F)—C | | 5.0% |
| 3O1-BEB(F)—C | | 12.0% |
| 5O1-BEB(F)—C | | 4.0% |
| 1V2-BEB(F,F)—C | | 16.0% |
| 3-HB—O2 | | 10.0% |
| 3-HH-4 | | 3.0% |
| 3-HHB—F | | 3.0% |
| 3-HHB—O1 | | 4.0% |
| 3-HBEB—F | | 4.0% |
| 3-HHEB—F | | 7.0% |
| 5-HHEB—F | | 7.0% |
| 3-H2BTB-2 | | 4.0% |
| 3-H2BTB-3 | | 4.0% |
| 3-H2BTB-4 | | 4.0% |
| 3-HB(F)TB-2 | | 5.0% |

Characteristics of this composition were determined to be as follows:

$T_{NI}$=92.8° C.

η=41.1 mPa.s

Δn=0.142

Δε=28.4

$V_{th}$=1.02 V

EXAMPLE 15

Composition Example 13

Liquid crystal composition comprising the following compounds in the amount shown below was prepared:

| | | |
|---|---|---|
| 3-H—VCOOH | (No. 2) | 5.0% |
| 5-H—VCOOH | (No. 4) | 5.0% |
| 3-H—VC | (No. 12) | 3.0% |
| 2-BEB—C | | 12.0% |

-continued

| | | |
|---|---|---|
| 3-BEB—C | | 4.0% |
| 4-BEB—C | | 6.0% |
| 3-HB—C | | 28.0% |
| 3-HEB—O4 | | 11.0% |
| 4-HEB—O2 | | 7.0% |
| 5-HEB—O1 | | 7.0% |
| 3-HEB—O2 | | 5.0% |
| 5-HEB—O2 | | 4.0% |
| 3-HHB—O1 | | 3.0% |

Characteristics of this composition were determined to be as follows:

$T_{NI}$=60.9° C.

η=26.8 mPa.s

Δn=0.113

Δε=10.3

$V_{th}$=1.32 V

EXAMPLE 16

Composition Example 14

Liquid crystal composition comprising the following compounds in the amount shown below was prepared:

| | | |
|---|---|---|
| 3-H—VCOOH | (No. 2) | 7.0% |
| 5-H—VCOOH | (No. 4) | 6.0% |
| 2-BEB—C | | 10.0% |
| 5-BB—C | | 12.0% |
| 7-BB—C | | 7.0% |
| 1-BTB-3 | | 7.0% |
| 2-BTB-1 | | 10.0% |
| 1O-BEB-2 | | 10.0% |
| 1O-BEB-5 | | 12.0% |
| 2-HHB-1 | | 4.0% |
| 3-HHB—F | | 4.0% |
| 3-HHB-1 | | 7.0% |
| 3-HHB—O1 | | 4.0% |

Characteristics of this composition were determined to be as follows:

$T_{NI}$=69.4° C.

η=20.9 mPa.s

Δn=0.161

Δε=6.6

$V_{th}$=1.80 V

EXAMPLE 17

Composition Example 15

Liquid crystal composition comprising the following compounds in the amount shown below was prepared:

| | | |
|---|---|---|
| 3-H—VCOOH | (No. 2) | 8.0% |
| 5-H—VCOOH | (No. 4) | 7.0% |
| 1V2-BEB(F,F)—C | | 8.0% |
| 3-HB—C | | 10.0% |
| V2V—HB—C | | 14.0% |
| V2V—HH-3 | | 19.0% |
| 3-HB—O2 | | 4.0% |
| 3-HHB-1 | | 10.0% |
| 3-HB(F)TB-2 | | 4.0% |
| 3-HB(F)TB-3 | | 4.0% |

-continued

| | | |
|---|---|---|
| 3-H2BTB-2 | | 4.0% |
| 3-H2BTB-3 | | 4.0% |
| 3-H2BTB-4 | | 4.0% |

Characteristics of this composition were determined to be as follows:

$T_{NI}$=104.9° C.

η=18.0 mPa.s

Δn=0.132

Δε=8.0

$V_{th}$=2.13 V

EXAMPLE 18

Composition Example 16

Liquid crystal composition comprising the following compounds in the amount shown below was prepared:

| | | |
|---|---|---|
| 3-H—VCOOH | (No. 2) | 6.0% |
| V2-H—VCOOH | (No. 7) | 5.0% |
| 5-BTB(F)TB-3 | | 10.0% |
| V2-HB—TC | | 10.0% |
| 3-HB—TC | | 10.0% |
| 3-HB—C | | 10.0% |
| 5-HB—C | | 7.0% |
| 5-BB—C | | 3.0% |
| 2-BTB-1 | | 10.0% |
| 2-BTB—O1 | | 5.0% |
| 3-HH-4 | | 5.0% |
| 3-HHB-1 | | 10.0% |
| 3-H2BTB-2 | | 3.0% |
| 3-H2BTB-3 | | 3.0% |
| 3-HB(F)TB-2 | | 3.0% |

Characteristics of this composition were determined to be as follows:

$T_{NI}$=104.8° C.

η=14.7 mPa.s

Δn=0.207

Δε=6.9

$V_{th}$=2.12 V

EXAMPLE 19

Composition Example 17

Liquid crystal composition comprising the following compounds in the amount shown below was prepared:

| | | |
|---|---|---|
| 3-H—VCOOH | (No. 2) | 7.0% |
| 1V2-BEB(F,F)—C | | 6.0% |
| 3-HB—C | | 18.0% |
| 2-BTB-1 | | 10.0% |
| 5-HH—VFF | | 30.0% |
| 1-BHH—VFF | | 8.0% |
| 1-BHH-2VFF | | 4.0% |
| 3-H2BTB-2 | | 5.0% |
| 3-H2BTB-3 | | 4.0% |
| 3-H2BTB-4 | | 4.0% |
| 3-HHB-1 | | 4.0% |

Characteristics of this composition were determined to be as follows:

$T_{NI}$=83.1° C.
$\eta$=12.9 mPa.s
$\Delta n$=0.131
$\Delta\epsilon$=6.5
$V_{th}$=2.10 V

EXAMPLE 20

Composition Example 18

Liquid crystal composition comprising the following compounds in the amount shown below was prepared:

| | | |
|---|---|---|
| 3-H—VCOOH | (No. 2) | 5.0% |
| 5-H—VCOOH | (No. 4) | 5.0% |
| V2-H—VCOOH | (No. 7) | 4.0% |
| 2-HB—C | | 5.0% |
| 3-HB—C | | 12.0% |
| 3-HB—O2 | | 15.0% |
| 2-BTB-1 | | 3.0% |
| 3-HHB-1 | | 8.0% |
| 3-HHB—F | | 4.0% |
| 3-HHB—O1 | | 5.0% |
| 3-HHEB—F | | 4.0% |
| 5-HHEB—F | | 4.0% |
| 2-HHB(F)—F | | 7.0% |
| 3-HHB(F)—F | | 7.0% |
| 5-HHB(F)—F | | 7.0% |
| 3-HHB(F,F)—F | | 5.0% |

Characteristics of this composition were determined to be as follows:
$T_{NI}$=105.7° C.
$\eta$=19.0 mPa.s
$\Delta n$=0.102
$\Delta\epsilon$=4.7
$V_{th}$=2.56 V

EXAMPLE 21

Composition Example 19

Liquid crystal composition comprising the following compounds in the amount shown below was prepared:

| | | |
|---|---|---|
| 3-H—VCOOH | (No. 2) | 3.0% |
| 5-H—VCOOH | (No. 4) | 3.0% |
| 2-HHB(F)—F | | 17.0% |
| 3-HHB(F)—F | | 17.0% |
| 5-HHB(F)—F | | 16.0% |
| 2-H2HB(F)—F | | 10.0% |
| 3-H2HB(F)—F | | 5.0% |
| 5-H2HB(F)—F | | 4.0% |
| 2-HBB(F)—F | | 6.0% |
| 3-HBB(F)—F | | 6.0% |
| 5-HBB(F)—F | | 13.0% |

Characteristics of this composition were determined to be as follows:
$T_{NI}$=105.8° C.
$\eta$=25.4 mPa.s
$\Delta n$=0.096
$\Delta\epsilon$=4.8
$V_{th}$=2.28 V Optically active compound expressed by the formula (Op-8) described above in an amount of 0.3 part by weight was added to 100 parts by weight of the primary composition described just above to obtain a secondary composition, and characteristic of the secondary composition was determined to be as follows:
P=80 $\mu$m

EXAMPLE 22

Composition Example 20

Liquid crystal composition comprising the following compounds in the amount shown below was prepared:

| | | |
|---|---|---|
| 3-H—VCOOH | (No. 2) | 4.0% |
| 5-H—VCOOH | (No. 4) | 4.0% |
| V2-H—VCOOH | (No. 7) | 3.0% |
| 7-HB(F)—F | | 5.0% |
| 5-H2B(F)—F | | 5.0% |
| 3-HB—O2 | | 10.0% |
| 3-HH-4 | | 2.0% |
| 3-HH[5D,6D,7D]-4 | | 3.0% |
| 2-HHB(F)—F | | 10.0% |
| 3-HHB(F)—F | | 10.0% |
| 5-HH[5D,6D,7D]B(F)—F | | 10.0% |
| 3-H2HB(F)—F | | 5.0% |
| 2-HBB(F)—F | | 3.0% |
| 3-HBB(F)—F | | 3.0% |
| 5-HBB(F)—F | | 6.0% |
| 2-H2BB(F)—F | | 5.0% |
| 3-H2BB(F)—F | | 6.0% |
| 3-HHB—O1 | | 3.0% |
| 3-HHB-3 | | 3.0% |

Characteristics of this composition were determined to be as follows:
$T_{NI}$=91.6° C.
$\eta$=19.3 mPa.s
$\Delta n$=0.094
$\Delta\epsilon$=3.3
$V_{th}$=2.67 V

EXAMPLE 23

Composition Example 21

Liquid crystal composition comprising the following compounds in the amount shown below was prepared:

| | | |
|---|---|---|
| 3-H—VCOOH | (No. 2) | 3.0% |
| 3-H—VC | (No. 12) | 3.0% |
| 7-HB(F,F)—F | | 3.0% |
| 3-HB—O2 | | 4.0% |
| 2-HHB(F)—F | | 10.0% |
| 3-HHB(F)—F | | 10.0% |
| 5-HHB(F)—F | | 10.0% |
| 2-HBB(F)—F | | 9.0% |
| 3-HBB(F)—F | | 9.0% |
| 5-HBB(F)—F | | 16.0% |
| 2-HBB—F | | 4.0% |
| 3-HBB—F | | 4.0% |
| 3-HBB(F,F)—F | | 5.0% |
| 5-HBB(F,F)—F | | 10.0% |

Characteristics of this composition were determined to be as follows:
$T_{NI}$=83.3° C.
$\eta$=24.7 mPa.s
$\Delta n$=0.113

$\Delta\epsilon=6.1$ $V_{th}=1.96$ V

EXAMPLE 24

Composition Example 22

Liquid crystal composition comprising the following compounds in the amount shown below was prepared:

| | | |
|---|---|---|
| 3-H—VCOOH | (No. 2) | 5.0% |
| 7-HB(F,F)—F | | 5.0% |
| 3-H2HB(F,F)—F | | 12.0% |
| 4-H2HB(F,F)—F | | 5.0% |
| 3-HHB(F,F)—F | | 10.0% |
| 4-HHB(F,F)—F | | 5.0% |
| 3-HBB(F,F)—F | | 10.0% |
| 3-HHEB(F,F)—F | | 10.0% |
| 4-HHEB(F,F)—F | | 3.0% |
| 5-HHEB(F,F)—F | | 3.0% |
| 2-HBEB(F,F)—F | | 3.0% |
| 3-HBEB(F,F)—F | | 5.0% |
| 3-HBCF2OB(F,F)—F | | 3.0% |
| 3-HGB(F,F)—F | | 15.0% |
| 3-HHBB(F,F)—F | | 6.0% |

Characteristics of this composition were determined to be as follows:

$T_{NI}=82.4°$ C.

$\eta=34.1$ mPa.s $\Delta n=0.087$ $\Delta\epsilon=12.4$ $V_{th}=1.48$ V

EXAMPLE 25

Composition Example 23

Liquid crystal composition comprising the following compounds in the amount shown below was prepared:

| | | |
|---|---|---|
| 3-H—VCOOH | (No. 2) | 4.0% |
| V2-H—VCOOH | (No. 7) | 4.0% |
| 3-HB—CL | | 10.0% |
| 5-HB—CL | | 4.0% |
| 7-HB—CL | | 4.0% |
| 1O1-HH-5 | | 5.0% |
| 2-HBB(F)—F | | 8.0% |
| 3-HBB(F)—F | | 8.0% |
| 5-HBB(F)—F | | 14.0% |
| 4-HHB—CL | | 8.0% |
| 3-H2HB(F)—CL | | 4.0% |
| 3-HBB(F,F)—F | | 10.0% |
| 5-H2BB(F,F)—F | | 9.0% |
| 3-HB(F)VB-2 | | 4.0% |
| 3-HB(F)VB-3 | | 4.0% |

Characteristics of this composition were determined to be as follows:

$T_{NI}=94.7°$ C.

$\eta=21.1$ mPa.s $\Delta n=0.130$ $\Delta\epsilon=4.7$ $V_{th}=2.36$ V

EXAMPLE 26

Composition Example 23

Liquid crystal composition comprising the following compounds in the amount shown below was prepared:

| | | |
|---|---|---|
| 3-H—VCOOH | (No. 2) | 5.0% |
| 5-HB—F | | 12.0% |
| 6-HB—F | | 9.0% |
| 7-HB—F | | 7.0% |
| 2-HHB—OCF3 | | 7.0% |
| 3-HHB—OCF3 | | 7.0% |
| 4-HHB—OCF3 | | 7.0% |
| 3-HH2B—OCF3 | | 4.0% |
| 5-HH2B—OCF3 | | 4.0% |
| 3-HHB(F,F)—OCF3 | | 5.0% |
| 3-HBB(F)—F | | 10.0% |
| 5-HBB(F)—F | | 10.0% |
| 3-HH2B(F)—F | | 3.0% |
| 3-HB(F)BH-3 | | 3.0% |
| 5-HBBH-3 | | 3.0% |
| 3-HHB(F,F)—OCF2H | | 4.0% |

Characteristics of this composition were determined to be as follows:

$T_{NI}=88.1°$ C.

$\eta=15.7$ mPa.s $\Delta n=0.094$ $\Delta\epsilon=4.3$ $V_{th}=2.47$ V

EXAMPLE 27

Composition Example 25

Liquid crystal composition comprising the following compounds in the amount shown below was prepared:

| | | |
|---|---|---|
| 5-H—VCOOH | (No. 4) | 3.0% |
| V2-H—VCOOH | (No. 7) | 3.0% |
| 5-H4HB(F,F)—F | | 7.0% |
| 5-H4HB—OCF3 | | 15.0% |
| 3-H4HB(F,F)—CF3 | | 8.0% |
| 5-H4HB(F,F)—CF3 | | 8.0% |
| 3-HB—CL | | 6.0% |
| 5-HB—CL | | 4.0% |
| 2-H2BB(F)—F | | 5.0% |
| 3-H2BB(F)—F | | 10.0% |
| 5-HVHB(F,F)—F | | 5.0% |
| 3-HHB—OCF3 | | 3.0% |
| 3-H2HB—OCF3 | | 3.0% |
| V—HHB(F)—F | | 5.0% |
| 3-HHB(F)—F | | 5.0% |
| 5-HHEB—OCF3 | | 2.0% |
| 3-HBEB(F,F)—F | | 5.0% |
| 5-HH—V2F | | 3.0% |

Characteristics of this composition were determined to be as follows:

$T_{NI}=76.2°$ C.

$\eta=25.4$ mPa.s $\Delta n=0.097$ $\Delta\epsilon=7.8$ $V_{th}=1.80$ V

EXAMPLE 28

Composition Example 26

Liquid crystal composition comprising the following compounds in the amount shown below was prepared:

|  |  |  |
|---|---|---|
| 3-H—VCOOH | (No. 2) | 5.0% |
| 5-H—VCOOH | (No. 4) | 5.0% |
| 3-HH-5 |  | 3.0% |
| 3-HH-4 |  | 3.0% |
| 3-HH—O1 |  | 8.0% |
| 3-HH—O3 |  | 6.0% |
| 3-HB—O1 |  | 7.0% |
| 3-HB—O2 |  | 5.0% |
| 3-HB(2F,3F)—O2 |  | 10.0% |
| 5-HB(2F,3F)—O2 |  | 10.0% |
| 3-HHB(2F,3F)—O2 |  | 12.0% |
| 5-HHB(2F,3F)—O2 |  | 13.0% |
| 3-HHB(2F,3F)-2 |  | 4.0% |
| 2-HHB(2F,3F)-1 |  | 4.0% |
| 3-HHEH-3 |  | 5.0% |

Characteristics of this composition were determined to be as follows:

$T_{NI}=85.2°$ C.
$\Delta n=0.081$
$\Delta\epsilon=-3.2$

EXAMPLE 29

Composition Example 27

Liquid crystal composition comprising the following compounds in the amount shown below was prepared:

|  |  |  |
|---|---|---|
| 2-H—VCOOH | (No. 1) | 3.0% |
| 3-H—VCOOH | (No. 2) | 3.0% |
| 3-H—VC | (No. 12) | 5.0% |
| 3O—H—VCOOH |  | 4.0% |
| 2-HHB(F)—F |  | 2.0% |
| 3-HHB(F)—F |  | 2.0% |
| 5-HHB(F)—F |  | 2.0% |
| 2-HBB(F)—F |  | 6.0% |
| 3-HBB(F)—F |  | 6.0% |
| 5-HBB(F)—F |  | 10.0% |
| 2-H2BB(F)—F |  | 9.0% |
| 3-H2BB(F)—F |  | 9.0% |
| 3-HBB(F,F)—F |  | 20.0% |
| 5-HBB(F,F)—F |  | 14.0% |
| 1O1-HBBH-4 |  | 5.0% |

Optically active compound expressed by the formula (Op-5) described above in an amount of 0.25 part by weight was added to 100 parts by weight of the primary composition described just above to obtain a secondary composition.

EXAMPLE 30

Composition Example 28

Liquid crystal composition comprising the following compounds in the amount shown below was prepared:

|  |  |  |
|---|---|---|
| 1O1-H—VCOOH | (No. 9) | 3.0% |
| 3O—H—VCOOH |  | 4.0% |
| 5-HB—CL |  | 12.0% |
| 3-HH-4 |  | 7.0% |
| 3-HB—O2 |  | 20.0% |
| 3-H2HB(F,F)—F |  | 8.0% |
| 3-HHB(F,F)—F |  | 8.0% |
| 3-HBB(F,F)—F |  | 6.0% |
| 2-HHB(F)—F |  | 5.0% |
| 3-HHB(F)—F |  | 5.0% |
| 5-HHB(F)—F |  | 5.0% |
| 2-H2HB(F)—F |  | 2.0% |
| 3-H2HB(F)—F |  | 1.0% |
| 5-H2HB(F)—F |  | 2.0% |
| 3-HHBB(F,F)—F |  | 4.0% |
| 3-HBCF2OB—OCF3 |  | 4.0% |
| 5-HBCF2OB(F,F)—CF3 |  | 4.0% |

INDUSTRIAL APPLICABILITY

As described above, cyclohexane derivatives of the present invention are novel liquid crystalline compounds having a wide temperature range of liquid crystal phase, being excellent in miscibility with other liquid crystalline compounds, and being low in viscosity, low in toxity, and safe.

Accordingly, compositions for liquid crystal display device which are improved particularly in the steepness and visual angle, and are considerably improved in driving temperature range can be achieved by using the liquid crystalline compound of the present invention as component of liquid crystal compositions.

What is claimed is:

1. A cyclohexane derivative expressed by the general formula (1)

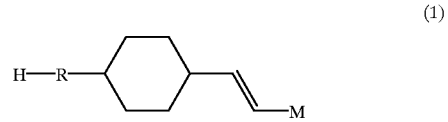

wherein R represents an alkylene chain having 2 to 10 carbon atoms in which alkylene chain, ethylene group (—CH$_2$CH$_2$—) may be replaced by ethenylene group (—CH═CH—) or methylenoxy group (—OCH$_2$—); and M represents COOH or CN group.

2. The cyclohexane derivative according to claim 1 wherein M is COOH group.

3. The cyclohexane derivative according to claim 1 wherein M is CN group.

4. The cyclohexane derivative according to claim 1 wherein R is an alkylene chain having 2 to 10 carbon atoms.

5. The cyclohexane derivative according to claim 2 wherein R is an alkylene chain having 2 to 10 carbon atoms.

6. The cyclohexane derivative according to claim 1 wherein R is an alkenylene group having 2 to 10 carbon atoms.

7. A liquid crystal composition comprising at least two components, at least one of which is a cyclohexane derivative defined in any one of claims 1 to 6.

8. A liquid crystal composition comprising, as a first component, at least one cyclohexane derivative defined in any one of claims 1 to 6, and comprising, as a second component, at least one compound selected from the group consisting of the compounds expressed by any one of the general formulas (2), (3), and (4)

(2)

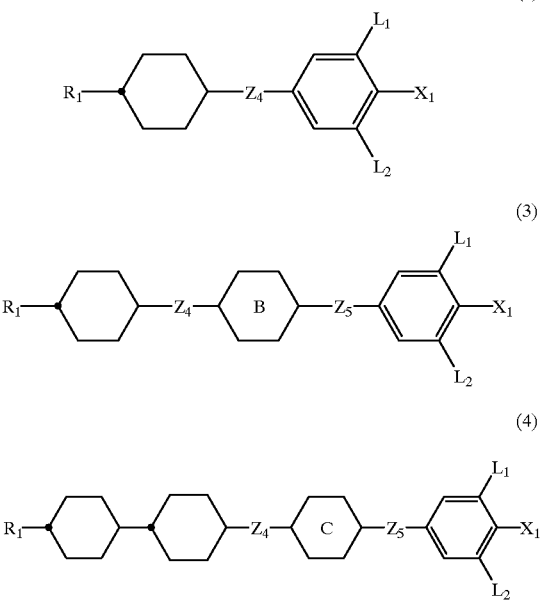

(3)

(4)

wherein $R_1$, $X_1$, $L_1$, $L_2$, $Z_4$, $Z_5$ may be the same or different among the formulas; $R_1$ represents an alkyl group having 1 to 10 carbon atoms in which alkyl group one or not adjacent two or more methylene groups may be replaced by oxygen atom or —CH═CH—, and any hydrogen atom may be replaced by fluorine atom; $X_1$ represents fluorine atom, chlorine atom, $OCF_3$, $OCF_2H$, $CF_3$, $CF_2H$, $CFH_2$, $OCF_2CF_2H$, or $OCF_2CFHCF_3$; $L_1$ and $L_2$ independently represent hydrogen atom or fluorine atom; $Z_4$ and $Z_5$ independently represent 1,2-ethylene group, 1,4-butylene group, —COO—, —CF$_2$O—, —OCF$_2$—, —CH═CH—, or a covalent bond; ring B represents trans-1,4-cyclohexylene or 1,3-dioxane-2,5-diyl, or 1,4-phenylene in which hydrogen atom on the ring may be replaced by fluorine atom; ring C represents trans-1,4-cyclohexylene, or 1,4-phenylene in which hydrogen atom on the ring may be replaced by fluorine atom; and each of the atoms which constitute these compounds may be selected from its isotopes.

9. A liquid crystal composition comprising, as a first component, at least one cyclohexane derivative defined in any one of claims 1 to 6, and comprising, as a second component, at least one compound selected from the group consisting of the compounds expressed by the general formula (5) or (6)

(5)

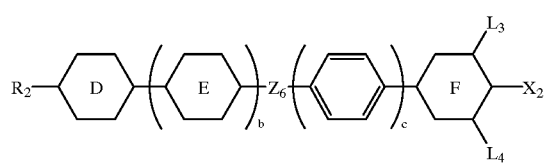

(6)

wherein $R_2$ and $R_3$ independently represent an alkyl group having 1 to 10 carbon atoms in which alkyl group one or not-adjacent two or more methylene groups may be replaced by oxygen atom or —CH═CH—, and any hydrogen atom may be replaced by fluorine atom; $X_2$ represents —CN group or —C≡C—CN group; ring D represents trans-1,4-cyclohexylene, 1,4-phenylene, 1,3-dioxane-2,5-diyl, or pyrimidine-2,5-diyl; ring E represents trans-1,4-cyclohexylene, 1,4-phenylene in which hydrogen atom on the ring may be replaced by fluorine atom, or pyrimidine-2,5-diyl; ring F represents trans-1,4-cyclohexylene or 1,4-phenylene; $Z_6$ represents 1,2-ethylene group, —COO—, or a covalent bond; $L_3$, $L_4$, and $L_5$ independently represent hydrogen atom or fluorine atom; b, c, and d are independently 0 or 1; and in the compounds of each formulas, each atom which constitutes those compounds may be selected from its isotopes.

10. A liquid crystal composition comprising, as a first component, at least one cyclohexane derivative defined in any one of claims 1 to 6, comprising, as a second component, at least one compound selected from the group consisting of the compounds expressed by any one of the general formulas (2), (3), and (4)

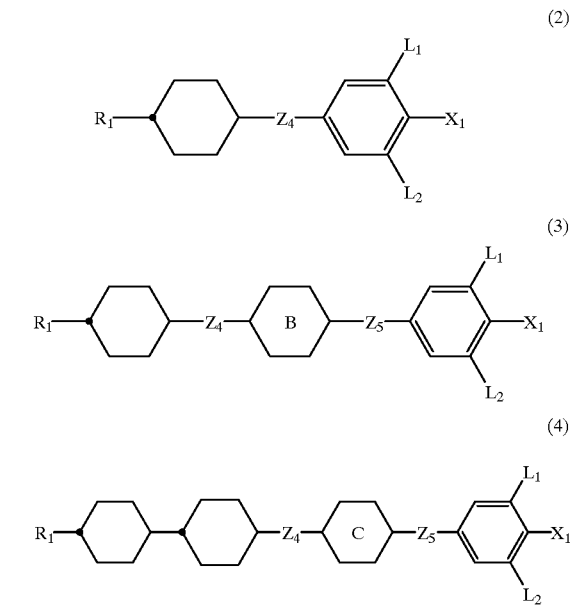

wherein $R_1$, $X_1$, $L_1$, $L_2$, $Z_4$, $Z_5$ may be the same or different among the formulas; $R_1$ represents an alkyl group having 1 to 10 carbon atoms in which alkyl group one or not adjacent two or more methylene groups may be replaced by oxygen atom or —CH═CH—, and any hydrogen atom may be replaced by fluorine atom; $X_1$ represents fluorine atom, chlorine atom, $OCF_3$, $OCF_2H$, $CF_3$, $CF_2H$ $CFH_2$, $OCF_2CF_2H$, or $OCF_2CFHCF_3$; $L_1$ and $L_2$ independently represent hydrogen atom or fluorine atom; $Z_4$ and $Z_5$ independently represent 1,2-ethylene group, 1,4-butylene group, —COO—, —CF$_2$O—, —OCF$_2$—, —CH=CH—, or a covalent bond; ring B represents trans-1,4-cyclohexylene or 1,3-dioxane-2,5-diyl, or 1,4-phenylene in which hydrogen atom on the ring may be replaced by fluorine atom; ring C represents trans-1,4-cyclohexylene, or 1,4-phenylene in which hydrogen atom on the ring may be replaced by fluorine atom; and in the compounds of each formulas, each of the atoms which constitute those compounds may be selected from its isotopes, and comprising, as a third component, at least one compound selected from the group consisting of the compounds expressed by any one of the general formulas (7), (8), and (9)

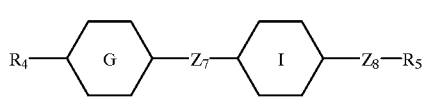

(7)

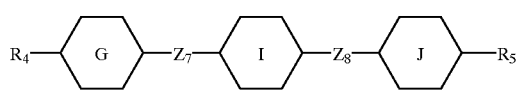

(8)

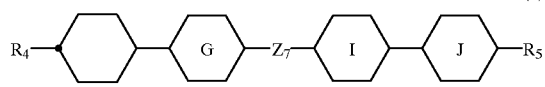

(9)

wherein R$_4$, R$_5$, ring G, ring I, and ring J may be the same or different among the of the formulas; R$_4$ and R$_5$ independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; ring G, ring I, and ring J independently represent trans-1,4-cyclohexylene or pyrimidine-2,5-diyl, or 1,4-phenylene in which hydrogen atom on the ring may be replaced by fluorine atom; Z$_7$ and Z$_8$ independently represent —C≡C—, —COO—, —CH$_2$CH2—, —CH=CH—, or a covalent bond; and in the compounds of each formulas, each atom which constitutes those compounds may be selected from its isotopes.

11. The liquid crystal composition according to claim 7 wherein the liquid crystal composition further comprises an optically active compound.

12. A liquid crystal display device comprising a liquid crystal composition defined in claim 7.

13. A liquid crystal composition comprising, as a first component, at least one cyclohexane derivative defined in any one of claims 1 to 6, comprising, as a second component, at least one compound selected from the group consisting of the compounds expressed by the formula (5) or (6)

(5)

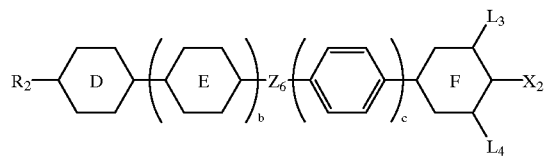

-continued (6)

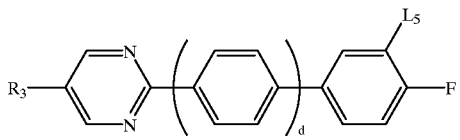

wherein R$_2$ and R$_3$ independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; X$_2$ represents —CN group or —C≡C—CN group; ring D represents trans-1,4-cyclohexylene, 1,4-phenylene, 1,3-dioxane-2,5-diyl, or pyrimidine-2,5-diyl; ring E represents trans-1,4-cyclohexylene, 1,4-phenylene in which hydrogen atom on the ring may be replaced by fluorine atom, or pyrimidine-2,5-diyl; ring F represents trans-1,4-cyclohexylene or 1,4-phenylene; Z$_6$ represents 1,2-ethylene group, —COO—, or a covalent bond; L$_3$, L$_4$, and L$_5$ independently represent hydrogen atom or fluorine atom; b, c, and d are independently 0 or 1; and in the compounds of each formulas, each atom which constitutes those compounds may be selected from its isotopes, and comprising, as a third component, at least one compound selected from the group consisting of the compounds expressed by any one of the general formulas (7), (8), and (9)

(7)

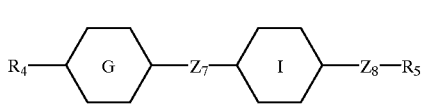

(8)

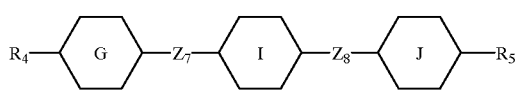

(9)

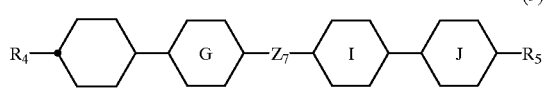

wherein R$_4$, R$_5$, ring G, ring I, and ring J may be the same or different among the of the formulas; R$_4$ and R$_5$ independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; ring G, ring I, and ring J independently represent trans-1,4-cyclohexylene or pyrimidine-2,5-diyl, or 1,4-phenylene in which hydrogen atom on the ring may be replaced by fluorine atom; Z$_7$ and Z$_8$ independently represent —C≡C—, —COO—, —CH$_2$CH$_2$—, —CH=CH—, or a covalent bond; and in the compounds of each formulas, each atom which constitutes those compounds may be selected from its isotopes.

14. A liquid crystal composition comprising, as a first component, at least one cyclohexane derivative defined in any one of claims 1 to 6, comprising, as a part of a second component, at least one compound selected from the group consisting of the compounds expressed by any one of the general formulas (2), (3), and (4)

(2)

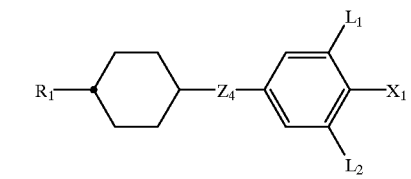

(3)

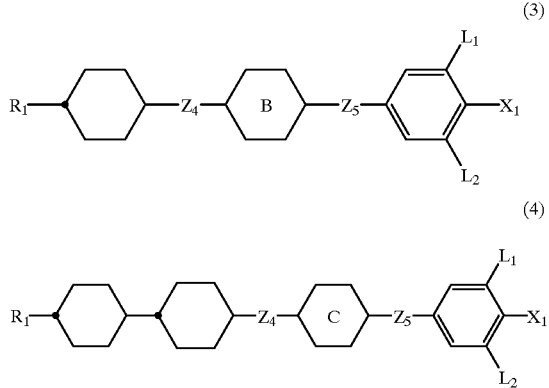

(4)

wherein $R_1$, $X_1$, $L_1$, $L_2$, $Z_4$, $Z_5$ may be the same or different among the formulas; $R_1$ represents an alkyl group having 1 to 10 carbon atoms in which alkyl group one or not adjacent two or more methylene groups may be replaced by oxygen atom or —CH=CH—, and any hydrogen atom may be replaced by fluorine atom; $X_1$ represents fluorine atom, chlorine atom, $OCF_3$, $OCF_2H$, $CF_3$, $CF_2H$, $CFH_2$, $OCF_2CF_2H$, or $OCF_2CFHCF_3$; $L_1$ and $L_2$ independently represent hydrogen atom or fluorine atom; $Z_4$ and $Z_5$ independently represent 1,2-ethylene group, 1,4-butylene group, —COO—, —CF$_2$O—, —OCF$_2$—, —CH=CH—, or a covalent bond; ring B represents trans-1,4-cyclohexylene or 1,3-dioxane-2,5-diyl, or 1,4-phenylene in which hydrogen atom on the ring may be replaced by fluorine atom; ring C represents trans-1,4-cyclohexylene, or 1,4-phenylene in which hydrogen atom on the ring may be replaced by fluorine atom; and each of the atoms which constitute these compounds may be selected from its isotopes, comprising as another part of the second component, at least one compound selected from the group consisting of the compounds expressed by the formula (5) or (6)

(5)

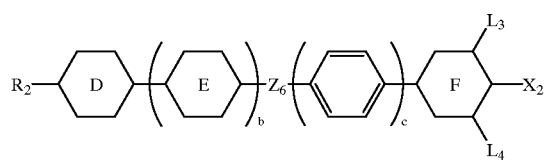

-continued (6)

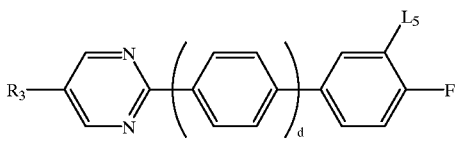

wherein $R_2$ and $R_3$ independently represent. an alkyl group having 1 to 10 carbon atoms in which alkyl group one or not-adjacent two or more methylene groups may be replaced by oxygen atom or —CH=CH—, and any hydrogen atom may be replaced by fluorine atom; $X_2$ represents —CN group or —C≡C—CN group; ring D represents trans-1,4-cyclohexylene, 1,4-phenylene, 1,3-dioxane-2,5-diyl, or pyrimidine-2,5-diyl; ring E represents trans-1,4-cyclohexylene, 1,4-phenylene in which hydrogen atom on the ring may be replaced by fluorine atom, or pyrimidine-2,5-diyl; ring F represents trans-1,4-cyclohexylene or 1,4-phenylene; $Z_6$ represents 1,2-ethylene group, —COO—, or a covalent bond; $L_3$, $L_4$, and $L_5$ independently represent hydrogen atom or fluorine atom; b, c, and d are independently 0 or 1; and in the compounds of each formulas, each atom which constitutes those compounds may be selected from its isotopes, and comprising, as a third component, at least one compound selected from the group consisting of the compounds expressed by any one of the general formulas (7), (8), and (9)

(7)

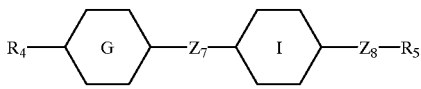

(8)

(9)

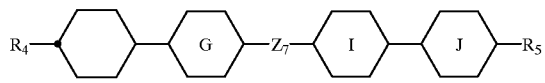

wherein $R_4$, $R_5$, ring G, ring I, and ring J may be the same or different among the of the formulas; $R_4$ and $R_5$ independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; ring G, ring I, and ring J independently represent trans-1,4-cyclohexylene or pyrimidine-2,5-diyl, or 1,4-phenylene in which hydrogen atom on the ring may be replaced by fluorine atom; $Z_7$ and $Z_8$ independently represent —C≡C—, —COO—, —CH$_2$CH$_2$—, —CH=CH—, or a covalent bond; and in the compounds of each formulas, each atom which constitutes those compounds may be selected from its isotopes.

* * * * *